United States Patent [19]

Blohm et al.

[11] 4,061,746

[45] Dec. 6, 1977

[54] LACTAMIMIDE INHIBITORS OF GASTROINTESTINAL HYPERSECRETION

[75] Inventors: Thomas R. Blohm; J. Martin Grisar; Norbert L. Wiech, all of Cincinnati, Ohio

[73] Assignee: Richardson-Merrell Inc., Wilton, Conn.

[21] Appl. No.: 679,810

[22] Filed: Apr. 23, 1976

[51] Int. Cl.² .................. A61K 31/33; A61K 31/445; A61K 31/38; A61K 31/40

[52] U.S. Cl. .................................... 424/244; 424/267; 424/274; 424/275; 424/282

[58] Field of Search .......................................... 424/244

[56] References Cited

U.S. PATENT DOCUMENTS 3,881,006   4/1975   Grisar et al. .......................... 424/244

*Primary Examiner*—Frederick E. Waddell
*Attorney, Agent, or Firm*—L. R. Hattan; E. O. Retter; G. W. Rauchfuss, Jr.

[57] ABSTRACT

A method of treating gastrointestinal hypersecretions which comprises administering substituted lactamimide derivatives.

51 Claims, No Drawings

LACTAMIMIDE INHIBITORS OF GASTROINTESTINAL HYPERSECRETION

FIELD OF INVENTION

This invention relates to a method of treating gastrointestinal hyperscretion by administration of lactamimide derivatives.

DESCRIPTION OF PRIOR ART

The compounds described herein are known, but to applicants' knowledge, the use of the compounds in the treatment of hypersecretion of the gastrointestinal tract has not been described heretofore. The compounds employed in this method have been described in the following patents: U.S. Pat. No. 3,894,002, issued July 8, 1975; U.S. Pat. No. 3,852,269 issued Dec. 3, 1974; Belgian Pat. No. 783,276 granted May 31, 1972; Belgian Pat. No. 798,188 granted Apr. 30, 1973; U.S. Pat. No. 3,873,520 issued Mar. 25, 1975; U.S. Pat. No. 3,803,170 issued Apr. 9, 1974; U.S. Pat. No. 3,838,151 issued Sept. 24, 1974; U.S. Pat. No. 3,833,559 issued Sept. 3, 1974; U.S. Pat. No. 3,783,162 issued Jan. 1, 1974; U.S. Pat. No. 3,900,565 issued Sept. 19, 1975; U.S. Pat. No. 3,881,006 issued Apr. 29, 1975; Belgian Pat. No. 814,114 granted May 15, 1974; U.S. Pat. No. 3,840,524 issued Oct. 8, 1974; U.S. Pat. No. 3,816,457 issued June 11, 1974; U.S. Pat. No. 3,890,445 issued June 17, 1975; U.S. Pat. No. 3,845,071 issued Oct. 29, 1974; U.S. Pat. No. 3,840,523 issued Oct. 8, 1974; Great Britian Pat. No. 1,201,848 issued Nov. 4, 1970; U.S. Pat. No. 3,378,438 issued Apr. 16, 1968.

SUMMARY OF INVENTION

Gastrointestinal hypersecretion can be inhibited or suppressed by the administration of a compound of the following general Formula, or a pharmaceutically acceptable salt thereof or the individual geometric or optical isomers where applicable:

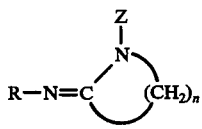

wherein Z is hydrogen or lower alkyl of from 1 to 4 carbon atoms; n is an integer of from 3 to 11; R is A. a straight or branched alkyl group of from 8 to 15 carbon atoms; or a lower alkoxyalkyl group wherein the alkyl moiety has from 8 to 15 carbon atoms and the alkoxy moiety has from 1 to 4 carbon atoms;

B. the group phenylaklylene wherein the alkylene moiety has from 1 to 6 carbon atoms and wherein the phenyl moiety is unsubstituted or substituted in which case the substituents may be attached at the ortho, meta or para-position of the phenyl ring and are chlorine, fluorine, bromine, lower alkyl having from 1 to 4 carbon atoms, lower alkoxy having from 1 to 4 carbon atoms, hydroxy or methylenedioxy;

C. the group

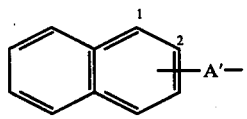

wherein A' is a straight or branched alkylene group of from 1 to 6 carbon atoms or benzyl and is attached to either the 1- or 2-position of the naphthyl ring which is unsubstituted or mono- or di- substituted with chlorine, fluorine, bromine, trifluoromethyl, a straight or branched alkyl group of from 1 to 12 carbon atoms, an alkoxy group of from 1 to 3 carbon atoms or $NO_2$;

D. the group 1- or 2-adamantyl or 1- or 2-norborny;

E. the group ortho, meta or para-biphenylyl;

F. the group 9-fluorenyl which is unsubstituted or substituted in which case the substituents may be attached to any one of the four available carbon atoms of each aromatic ring and are chlorine, bromine, fluorine, a lower alkyl group having from 1 to 4 carbon atoms, a lower alkoxy group having from 1 to 4 carbon atoms or $NO_2$;

G. dibenzocyclohepten-5-yl;

H. 1-benzylcyclopentyl;

I. the group

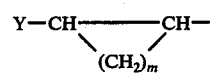

wherein m is an integer of from 1 to 6, and Y is 2-thienyl, a cycloalkyl group having from 5 to 7 carbon atoms, a phenyl group which is unsubstituted or substituted in which case the substituents may be attached to the ortho, meta, or para-position of the phenyl ring and are chlorine, fluorine, bromine, a lower alkyl group having from 1 to 4 carbon atoms or a lower alkoxy group having from 1 to 4 carbon atoms;

J. the group

wherein X is oxygen or sulfur, A is a bond or an alkylene chain of from 1 to 3 carbon atoms, and $R^1$ is hydrogen, a straight or branched lower alkyl group having from 1 to 4 carbon atoms, a straight or branched lower alkenyl group having from 3 to 6 carbon atoms, cycloalkyl of from 3 to 6 carbon atoms or phenyl;

K. the group

wherein $R^2$ is phenyl or a cycloalkyl group having from 3 to 6 carbon atoms, and $R^3$ is hydrogen or methyl;

L. the group

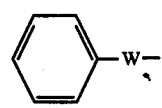

wherein W is a straight or branched divalent alkylene chain having from 2 to 6 carbon atoms which is substituted with one phenyl group on any of the 6 carbon atoms with the proviso that the carbon atom adjacent to the exocyclic nitrogen atom must have at least one hydrogen attached to it;

M. the group

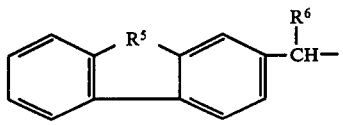

wherein $R^5$ is oxygen, sulfur, —CH$_2$—, —CH$_2$CH$_2$— or —CH=CH—, and $R^6$ is hydrogen or a lower alkyl group of from 1 to 4 carbon atoms;

N. the group

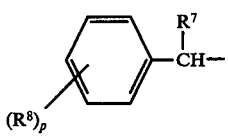

wherein $R^7$ is cycloalkyl of from 3 to 5 carbon atoms, $R^8$ is hydrogen, lower alkoxy of from 1 to 4 carbon atoms or lower alkyl of from 1 to 4 carbon atoms, and p is the integer 1 or 2;

O. the group

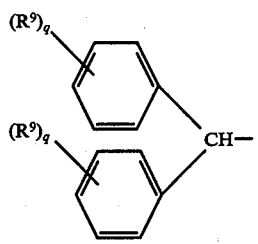

wherein $R^9$ is hydrogen, a straight or branched lower alkyl group of from 1 to 4 carbon atoms, chlorine, fluorine, bromine, CF$_3$, SCF$_3$, OCF$_3$, phenyl, phenoxy or a lower alkoxy group of from 1 to 4 carbon atoms and q is an integer of from 1 to 3;

P. the group

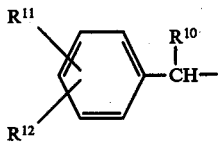

wherein $R^{10}$ is a lower alkyl group of from 1 to 4 carbon atoms, $R^{11}$ is hydrogen or lower alkyl of from 1 to 4 carbon atoms, $R^{12}$ is an alkyl group having from 8 to 14 carbon atoms, an alkoxy group having from 8 to 14 carbon atoms, a cycloalkyl group having from 5 to 14 carbon atoms, phenyl, phenoxy, phenylalkyl wherein the alkyl moiety has from 1 to 4 carbon atoms, phenylalkoxy wherein the alkoxy moiety has from 2 to 4 carbon atoms, 2,2-diphenylvinyl or fluoren-9-ylidene; or Q. the group

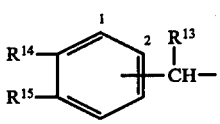

wherein the phenyl moiety is attached to the

moiety through the 1- or 2-position of the phenyl ring, $R^{13}$ is a lower alkyl group of from 1 to 4 carbon atoms and $R^{14}$ and $R^{15}$ taken together are (—CH$_2$—)$_3$, —CH$_2$CH$_2$C(CH$_3$)$_2$—, —(CH$_2$)$_4$— or —C(CH$_3$)$_2$CH$_2$CH$_2$C(CH$_3$)$_2$—; with the proviso that when R is the group

Z is hydrogen, and when R is 1-benzylcyclopentyl, Z is hydrogen and n is 3; and pharmaceutically acceptable acid addition salts thereof.

DETAILED DESCRIPTION OF INVENTION

It is apparent from the foregoing general Formula I that all of the compounds utilized in the instantly claimed invention contain a lactamimide ring having the structure

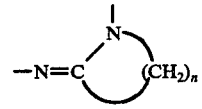

wherein $n$ is an integer of from 3 to 11. Thus, the heterocyclic ring of the lactamimide moiety can be pyrrolidine, piperidine, hexahydroazepine, octahydroazocine, octahydroazonine, azacyclodecane, azacycloundecane, azacyclododecane or azacyclotridecane each of which is attached to the exocyclic nitrogen of the lactamimide moiety through the 2-position.

For convenience and uniformity the compounds described herein are represented and named as substituted 2-iminoperhydroazacarbocyclics, as represented by general Formula I. It is known that compounds of this type as acid addition salts may also be represented by the tautomeric form illustrated by the following general Formula II;

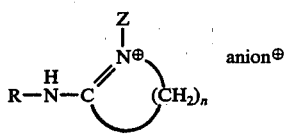

Formula II

This tautomerism has been discussed by R. Kwok and P. Pranc, J. Org. Chem. 32, 740 (1967). Structures of this formula could be named differently. In solution under the conditions of the therapeutic utility the proportions of each tautomeric form or the delocalization of the charge between the two nitrogen atoms will be dependent upon numerous factors including the nature of the substituents and the pH of the medium. This equilibrium state is conveniently illustrated by the following general Formula III;

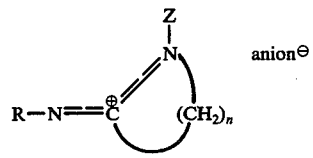

Formula III

The compounds of general Formula I wherein R is other than the group

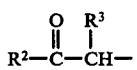

as acid addition salts can exist in either tautomeric form, and it is understood that this invention relates to the use of compounds represented or named in either tautomeric form. In the above general Formulas II and III, the various symbols R, Z and n have the meanings defined in general Formula I.

Compounds of general Formula I wherein R represents

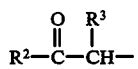

and Z represents hydrogen may exist in a cyclic form as represented by the following general Formula IV and be in equilibrium therewith.

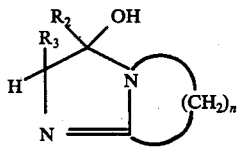

Formula IV

In the above general Formula IV the various symbols n, $R_2$, $R_3$ and $R_4$ have the meanings defined in general Formula I. It is understood that this invention embraces the use of the compounds of general Formula I wherein R is the group

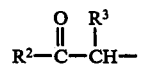

when in the form as represented by general Formula IV. For purposes of convenience the compounds of this type are named herein as the cyclic form.

It is known in the art that inhibition of adenylate cyclase results in the suppression or inhibition of hypersecretion of fluid in the small intestine (*Advances in Cyclic Nucleotide Research, Vol.* 1: Physiology and Pharmacology of Cyclic AMP, Raven Press Publishers, New York, pp. 171-2 (1972)) as well as hypersecretion of hydrochloric acid in the stomach J.Clin.Invest. 53, 334-7 (1974). It has been discovered that the compounds of general Formula I are inhibitors of adenylate cyclase activity rendering them useful in the treatment or inhibition of hypersecretion of gastric hydrochloric acid and fluids from the small intestine. The utility of the compounds of general Formula I as inhibitors of gastrointestinal secretions has been demonstrated in other test systems. For example, 2-[cis-2-phenylcyclopentyl)imino]azacyclotridecane hydrochloride has been shown to possess anti-secretory activity in the perfused rabbit intestinal loop exposed to cholera toxin and has been demonstrated to exhibit an antigastric acid secretory effect in the pylorus ligated rat, which is a modification of the Shay rat preparation, H. Shay, et al., Gastroenterology 5, 43 (1945). This compound also resulted in the inhibition of acid output induced by histamine, pentagastrin and 2-deoxy-D-glucose in the perfused rat stomach.

As used herein, the term gastrointestinal hypersecretion is intended to mean hypersecretion of fluid in the small intestine and hypersecretion of fluid in the stomach or gut, particularly hydrochloric acid and pepsin, collectively referred to as gastric fluid hypersecretion. The compounds of general Formula I are useful in the treatment of gastrointestinal ulcers, that is, ulcers of the gut and duodenum, and diarrhea mediated by enterotoxins, such as, *Vibrio cholera, Escherichia coli, Shigella* species, *Salmonella, Clostridium,* and *Klebsiella* species, diarrhea mediated by a viral agent, such as, orbivirus, and also, diarrhea resulting from administration of antibiotics. The compounds of general Formula I may be administered to warm blooded animals including mammals, such as, dogs, cats, rats, horses, bovine cows, mice, pigs, goats, sheep and humans and birds, such as, chickens and turkeys. The compounds may be administered alone or may be used in combination with antibiotics, such as, antibacterial agents, for example, clindamycin, lincomycin, tetracycline and cephalosporins used in general therapy or for the treatment of the enterotoxins. The compounds may also be used with other antisecretory agents, such as, diphenoxylate and atropine, and with electrolyte solutions serving as fluid replacement or maintenance therapy. The compounds of general Formula I may be administered alone or in the form of pharmaceutical preparations and may be administered orally or parenterally, for example, intravenously and intraperitoneally. Pharmaceutical preparations containing conventional pharmaceutical carriers and as active ingredients, compounds of general Formula I can be employed in unit dosage forms such as, solids, for example, tablets, capsules and pills or liquid solutions, suspensions and emulsions for oral and parenteral administration. The amount of compound administered can be any gastrointestinal hypersecretion inhibitory effective amount or any gastric or intestinal hypersecretion inhibitory effective amount which amounts would be effective in treating ulcers or diarrhea, that is, an anti-ulcer or anti-diarrheal effective amount. The dosage unit administered can vary over a wide range to provide from about 0.1 mg/kg (milligram per kilogram) to 250 mg/kg of body weight of the patient per day, and preferably from about 1 mg/kg to 100 mg/kg of body weight of the patient per day to achieve the desired effect. Unit doses may contain from 5 mg to 500 mg of the compound of general Formula I and may be administered, for example, from 1 to 4 times daily. In addition, the compounds of general Formula I may also be administered on alternate days or series of days and may be administered alone or concurrently, sequentially or serially with other agents as mentioned above. As used herein, the term patient is intended to mean the animal or mammal being treated. Illustrative examples of suitable pharmaceutical preparations of the compounds of general Formula I are the following.

An illustrative composition for tablets is the following:

|     |                                                       | mg/tablet |
|-----|-------------------------------------------------------|-----------|
| (a) | 2-[(cis-2-phenylcyclopentyl)-inino]azacyclotridecane HCl | 15        |
| (b) | Lactose                                               | 33        |
| (c) | Corn starch                                           | 11.25     |
| (d) | Sucrose 3% starch                                     | 12.75     |
| (e) | Corn starch paste (10%)                               | 1.50      |
| (f) | Zinc stearate                                         | 1.50      |

The dry lactose, corn starch and sucrose 3% starch are screened through a 30-mesh screen and blended. The powder mix is granulated with 10% corn starch paste, and the wet granulation is passed through a No. 4 screen and dried. The dried granulation is screened and blended with the zinc sterate which also is screened, and the resulting mixture is compressed into tablets weighing 75 mg each.

An enteric coated tablet is afforded when a tablet formulated as above is sprayed with a 4% solution of hydroxypropyl methylcellulose phthalate increasing the weight of the tablet about 6 mg.

An illustrative sterile aqeuous solution suitable for parenteral use is prepared from the following ingredients:

| | | Grams |
|---|---|---|
| (a) | 2-[(diphenylmethyl)imino]-pyrrolidine HCl | 1 |
| (b) | Polyethylene glycol 4000, U.S.P. | 3 |
| (c) | Sodium chloride | 0.9 |
| (d) | Polyoxyethylene derivatives of sorbitan monooleate (TWEEN 80) U.S.P. | 0.4 |
| (e) | Sodium metabisulfite | 0.1 |
| (f) | Methylparaben, U.S.P. | 0.18 |
| (g) | Propylparaben, U.S.P. | 0.02 |
| (h) | Water for injection q.s. to 100 ml | |

The parabens, sodium metabisulfite and sodium chloride are dissolved in approximately one-half the volume of water for injection at 80° C with stirring. The solution is cooled to below 40° C and the active ingredient is dissolved therein followed by the polyethylene glycol 4,000 and the polyoxyethylene derivatives of sorbitan monooleate. The cooled solution is adjusted to the final volume with water for injection and is then sterilized by sterile filtration through a suitable filter. Each one ml of solution contains 10 mg of the active ingredient.

An illustrative capsule preparation is the following. One thousand two-piece hard gelatin capsules for oral use each containing 100 mg of the active ingredient are prepared from the following ingredients:

| | | Grams |
|---|---|---|
| (a) | 2-[(2-cyclohexylcyclopentyl)imino]-hexahydroazepine HCl | 100 |
| (b) | Lactose, U.S.P. | 100 |
| (c) | Starch, U.S.P. | 10 |
| (d) | Talc, U.S.P. | 5 |
| (e) | Calcium stearate | 1 |

The finely powdered materials are mixed until uniformly dispersed and filtered into hard shelled gelatin capsules of the appropriate size.

In a similar fashion one-piece soft gelating capsules can be prepared in which the above formulation can be granulated slugged or compressed directly into a rotary die or plate mold in which the capsule is formed. Alternatively, the above excipients may be omitted and the active ingredient dispensed as a powder directly into the capsule.

A preferred embodiment of this invention is the use of the compounds described herein wherein $n$ is an integer of from 5 to 11, and within this preferred embodiment the use of the compounds wherein n is the integer 11 is more preferred. Another preferred embodiment of this invention is the use of the compounds described herein wherein n is the integer 3. Another preferred embodiment of this invention is the use of the compounds described herein wherein n is the integer 4.

The most preferred embodiment of this invention is the use of the compounds of general Formula I having the structure

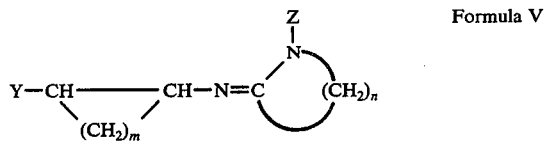

Formula V wherein the various substituents Y, Z, m and n have the meanings defined in general Formula I. Within this most preferred embodiment the use of the compounds of Formula V wherein n is an integer of from 5 to 11 is particularly preferred with the use of the compounds wherein $n$ is 11 being especially preferred.

Illustrative examples of compounds of Formula V are hexahydro-2-[(trans-2-phenylcyclopentyl)imino]azepine, 2-[2-([p-chlorophenyl]cyclopentyl)imino]hexahydroazepine, 1-butylhexahydro-2-[(cis-2-phenylcyclopentyl)imino]azepine, hexahydro-2-[2([o-tolyl]cyclohexyl)imino]azepine, 2-[2-([m-anisyl]cyclohexyl)imino]azacyclododecane, 2-[(2-phenylcyclopentyl)imino]azacyclotridecane, 2-[(2-phenylcycloheptyl)imino]azacycloundecane, 2-[(2-cyclohexylcyclopentyl)-imino]hexahydroazepine, hexahydro-2-[(trans-2-phenylcyclopropyl)imino]azepine, 2-(2-phenylcyclopropylimino)azacyclotridecane, 2-[(2-phenylcyclopentyl)imino]piperidine, octahydro-2-[(2-phenylcyclobutyl)imino]azonine, 2-[(2-[2-thienyl]cyclopentyl)imino]pyrrolidine and 2-[(2-cyclohexylcyclopentyl)imino]piperidine hydrochloride.

Other preferred embodiments of this invention are the use of the compounds set forth below as Formulas A to G and J to Q with the use of the compounds within each formula wherein $n$ is an integer of from 5 to 11 being more preferred and the use of the compounds wherein $n$ is the integer 11 being the most preferred:

Formula A wherein $R^{16}$ is a straight or branched alkyl group of from 8 to 15 carbon atoms, such as, octyl, nonyl, decyl, undecyl, dodecyl, tridecyl, tetradecyl, pentadecyl, and 3,7-dimethyloctyl, or a lower alkoxyalkyl group wherein the alkyl moiety has from 8 to 15 carbon atoms and the alkoxy moiety has from 1 to 4 carbon atoms, such as, 8-methoxyoctyl, 15-ethoxypentadecyl, 12-n-propoxydodecyl, 14-n-butoxytetradecyl, and 13-methoxytridecyl; Z is hydrogen or a lower alkyl group of from 1 to 4 carbon atoms; and n is an integer of from 3 to 11. Illustrative examples of compounds of Formula A are 2-(8-methoxyoctylimino)azcyclotridecane, 2-(12-n-propoxydodecylimino)azacyclododecane, hexyhydro-2-(10-butoxydecylimino)-azepine, 2-(11-ethoxyundecylimino)piperidine and 2-(12-n-propoxydodecylimino)pyrrolidine.

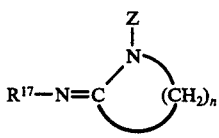

Formula B wherein $R^{17}$ is a phenylalkylene group wherein the alkylene moiety has from 1 to 6 carbon atoms, such as, methylene, ethylene, propylene, and butylene, and wherein the phenyl moiety is unsubstituted or substituted at the ortho, meta or para-position with chlorine, fluorine, bromine, a lower alkyl group of from 1 to 4 carbon atoms, such as, methyl, ethyl, n-propyl, or n-butyl, a lower alkoxy group of from 1 to 4 carbon atoms, such as, methoxy, ethoxy, or propoxy, hydroxy, or methylenedioxy which is attached to the phenyl ring at either the 3- and 4-positions or the 2- and 3-positions; Z is hydrogen or lower alkyl of from 1 to 4 carbon atoms; and n is an integer of from 3 to 11. Illustrative examples of compounds of Formula B are 2-(benzylimino)pyrrolidine, 2-(p-chlorobenzylimino)piperidine, hexahydro-2-(3′,4′-methylenedioxybenzylimino)azepine, 2-(p-tolylimino)azacyclodecane, octahydro-2-(p-anisylimino)azonine, octahydro-2-(p-n-butoxyphenethylimino)-azocine, hexahydro-2-(p-n-propylphenpentylimino)azepine, hexahydro-2-(o-tolylimino)azepine, and hexhydro-2-(benzylimino)azepine.

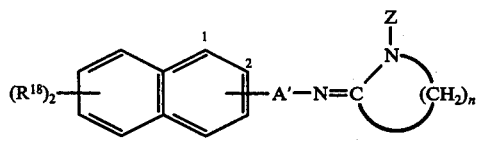

Formula C wherein A' is benzyl, or a straight or branched alkylene group of from 1 to 6 carbon atoms, such as, methylene, ethylene, propylene, butylene, and hexylene, and is attached to either the 1- or 2-position of the naphthlene ring; $R^{18}$ is hydrogen, chlorine, bromine, trifluoromethyl, an alkyl group of from 1 to 12 carbon atoms, such as, methyl, ethyl, n-butyl, hexyl, decyl, or dodecyl, an alkoxy group of from 1 to 3 carbon atoms, such as, methoxy, ethoxy, or propoxy, or $NO_2$; and Z and n have the meanings, defined in general Formula 1. Illustrative examples of compounds of Formula C are hexahydro-2-[1-(6-dodecyl-1-naphthyl)ethylimino]azepine, 2-(7-trifluoromethyl-2-naphthylmethylimino)octahydroazonine, hexahydro-2-(1-naphthylmethylimino)azepine, 2-[1-naphthyl)ethylimino]-piperidine, 2-(6-bromo-2-methoxy-1-naphthylmethylimino)-azacyclotridecane, 2[1-(5,8-dimethyl-1-naphthyl)ethylimino]-hexahydroazepine, 2-[1-(1naphthyl)ethylimino]octahydroazocine, and hexahydro-2-α-(1-naphthyl)benzylimino]azepine.

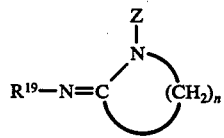

Formula D wherein $R^{19}$ is 1- or 2-adamantyl or 1- or 2-norbornyl, and Z and $n$ have the meanings defined in general Formula 1. Illustrative examples of compounds of Formula D are 2-(1-adamantylimino)azacyclotridecane, 2-(1-adamantylimino)-pyrrolidine, 2-(2-adamantyl)hexahydroazepine, 2-(1-adamantylimino)azacycloundecane, 1-methyl-2-(2-adamantylimino)azacyclododecane, 2-(2-adamantylimino)azacyclodecane, 2-(2-norbornylimino)azacyclododecane, 1-methyl-2-(1-norornylimino)azacyclodecane, 2-(2-norbornylimino)piperidine, 1-ethyl-2-(2-norbornylimino)hexahydroazepine, 2-(2-norbornylimino)pyrrolidine, and 2-(1-norbornylimino)azacyclotridecane.

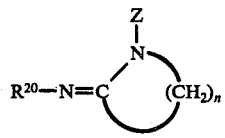

Formula E wherein $R^{20}$ is ortho, meta or para-biphenylyl, and Z and n have the meanings defined in general Formula 1. Illustrative examples of compounds of Formula E are 2-(o-biphenylylimino)azacyclotridecane, 2-(m-biphenylylimino)hexahydroazepine, 1-methyl-2-(p-biphenylylimino)piperidine and 2-(o-biphenylylimino)-pyrrolidine.

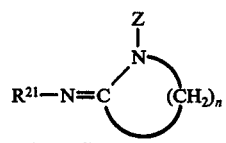

Formula F wherein $R^{21}$ is 9-fluorenyl which is unsubstituted or substituted in which case the substituents may be attached to any one of the 4 available carbon atoms in each aromatic ring and are chlorine, bromine, fluorine, a lower alkyl group of from 1 to 4 carbon atoms, such as, methyl, ethyl, n-propyl, or n-butyl, a lower alkoxy group of from 1 to 4 carbon atoms, such as, methoxy, ethoxy, n-propoxy, or n-butoxy, or $NO_2$; and Z and n have the meanings defined in general Formula 1. Illustrative examples of compounds of Formula F are 2-(9-fluorenylimino)azacyclotridecane, 2-(9-fluorenylimino)pyrrolidine, 2-(2-nitro-9-fluorenylimino)-piperidine, 2-(3-methoxy-9-fluorenylimino)hexahydroazepine, 2-(9-fluorenylimino)octahydroazepine, 2-(3,6-dimethyl-9-fluorenylimino)hexahydroazepine, 1-methyl-2-(9-fluorenylimino)azacyclotridecane, 2-(3-methyl-7-chloro-9-fluorenylimino)azacyclododecane, 2-(9-fluorenylimino)azacycloundecane, 2-(4-bromo-9-fluorenylimino)azacyclodecane, 2-(3-n-propoxy-9-fluorenylimino)pyrrolidine, and 2-(2-fluoro9-fluorenylimino)piperidine.

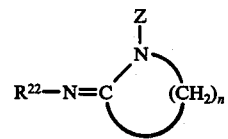

Formula G wherein $R^{22}$ is dibenzocycloheptan-5-yl, and Z and $n$ have the meanings defined in general Formula 1. Illustrative examples of compounds of Formula G are 2-[(10,11-dihydro-5H-dibenzo[a,d]cycloheptan-5-yl)imino]hexahydroazepine, 2-[(10,11-dihydro-5H-dibenzo[a,d]cycloheptan-5-yl)imino]-octahydroazocine, 2-[(10,11-dihydro-5H-dibenzo[a,d]cycloheptan-5-yl)imino]octahydroazonine, 20[(10,11-dihydro-5H-dibenzo[a,d]cycloheptan-5-yl)imino]azacyclotridecane, 2-[(10,11-dihydro-5H-dibenzo[a,d]cycloheptan-5-yl)imino]-azacyclododecane, 2-[(10,11-dihydro-5H-dibenzo[a,d]cycloheptan-5-yl)imino]piperidine, and 2-[(10,11-dihydro-5H-dibenzo[a,d]cycloheptan-5-yl)imino]pyrrolidine.

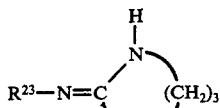

Formula H wherein R[23] is 1-benzylcyclopentyl, which compound is 2-[(1benzylcyclopentyl)imino]pyrrolidine,

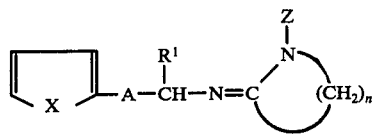

Formula J wherein X is oxygen or sulfur; A is a bond or an alkylene group of from 1 to 3 carbon atoms, such as, methylene, ethylene, and propylene; R[1] is hydrogen, a straight or branched lower alkyl group of from 1 to 4 carbon atoms, such as, methyl, ethyl, isopropyl and n-butyl, a lower alkenyl group having from 3 to 6 carbon atoms, such as, allyl and 2-butenyl, a cycloalkyl group of from 3 to 6 carbon atoms, such as, cyclopropyl, cyclobutyl, cyclopentyl, and cyclohexyl, or phenyl; Z and $n$ have the meanings defined in general Formula 1. Illustrative examples of compounds of Formula J are 2-[[α-(2-thienyl)-benzyl]imino]azacyclotridecane, 2-[(2-thenyl)imino]hexahydroazepine, 1-methyl-2-(2-thenylimino)-hexahydroazepine, hexahydro-2-[1-(2-thenyl)-propylimino]azepine, 2-(furfurylimino)hexahydroazepine, 2-[[α-(2-furyl)benzyl]imino]octahydroazocine, 1-ethyl-2- [[α-(2-furyl)benzyl]imino]octahydroazocine, 2- [[α-(2-thienyl)benzyl]imino]hexahydroazepine, 2-[1-(2-thenyl)propylimino]pyrrolidine, 2-[(α-cyclopropyl-2-thenyl)imino]hexahydroazepine, 2-[β-(2-thienyl)-isopropylimino]hexahydroazepine, 2-[2-(1-[2-thienyl]pent-4-enyl)imino]azacyclotridecane, 2-[2-(1-[2-furyl]pent-4-enyl)imino]azacyclododecane, 2-[(α-cyclopentyl-2-thenyl)-imino]piperidine, 2-[(α-[2-furyl]benzyl)imino]-hexahydroazapine, 2-[(3-[4-(2-furyl)-4-cyclopentyl]-butylimino)azepine, and 2-(2-[1-(2-furyl)hex-4-enyl]-imino)azacyclotridecane.

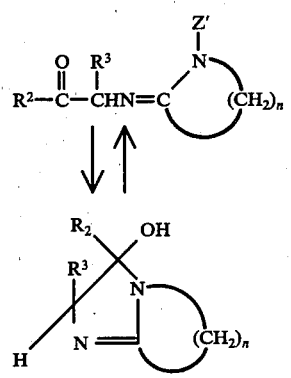

Formula K wherein R[2] is phenyl or cycloalkyl of from 3 to 6 carbon atoms, such as, cyclopropyl, cyclobutyl and cyclopentyl; R[3] is hydrogen or methyl; n has the meaning defined in general Formula I and Z' is hydrogen, Illustrative examples of compounds of Formula K are 2,3,5,6,7,8-hexahydro-2-methyl-3-phenylimidazo[1,2-a]pyridin-3-ol, 2,3,6,7-tetrahydro-2-methyl-3-phenyl-5H-pyrrolo[1,2-a]-imidazol-3-ol, 2,3,6,7-tetrahydro-2,2-dimethyl-3-phenyl-5H-pyrrolo[1,2,-a]imidazo-3-ol, 2,3,5,6,7,8,9,10-octahydro-2-methyl-3-phenylimidazo[1,2-a]azocine-3-ol, 2,3,5,6,7,8-hexahydro-3-phenylimidazo[1,2-a]pyridin-3-ol, 3-cyclohexyl-2,3,6,7,8,9-hexahydro-2-methyl-5H-imidazo[1,2-a]-azepine-3-ol.

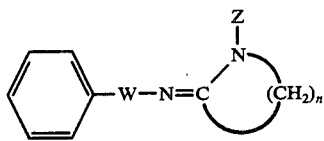

Formula L wherein W is a straight or branched divalent alkylene chain having from 2 to 6 carbon atoms which is substituted with one phenyl group on any of the 6 carbon atoms with the proviso that the carbon atom adjacent to the exocyclic nitrogen atom must have at least one hydrogen attached thereto; and Z and n have the meanings defined in general Formula I. Illustrative examples of straight or branched phenyl substituted divalent lower alkylene groups which W represents are 1-phenyl-1,1-ethylene, 1-phenyl-1,2-ethylene, 3-phenyl-1,3-propylene, 1-phenyl-1,2-propylene, 2-phenyl-1,4-butylene, and 3-phenyl-1,5-pentylene. Illustrative examples of compounds of Formula L are hexahydro-2-[(β-methyl-β-phenylphenethyl)imino]azepine, 2-[(β-ethyl-β-phenylphenethyl)imino]octahydroazocine, 2-[(1,5-diphenylpentyl)imino]octahydroazonine, 2-[(1,3-diphenylpropyl)-imino]piperidine, 2-(2,2-diphenylethylimino)hexahydroazepine, 2-(3,3-diphenylpropylimino)hexahydroazepine, 2-(2,3-diphenylpropylimino)azacyclotridecane, 2-[(α-methyl-β-phenylphenethyl)imino]hexahydroazepine, 2-(1,4-diphenylbutylimino)pyrrolidine, 1-methyl-2-(1,4-diphenylbutylimino)-azacyclododecane, 2-[(β-phenyl-β-propylphenenethyl)imino]-azacyclotridecane, 2-[(β-isopropyl-β-phenylphenethyl)imino]-hexahydroazepine, 2-(α-phenylphenethylimino)pyrrolidine, 2-[(α-methyl-β-phenylphenylpropyl)imino]octahydroazocine, 2-[(β-phenyl-β-propylphenethyl)imino]octahydroazonine.

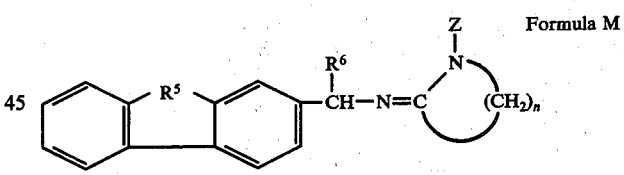

Formula M wherein R[5] is oxygen, sulfur, —CH$_2$—, —CH$_2$CH$_2$— or —CH=CH—; R[6] is hydrogen or a lower alkyl group of from 1 to 4 carbon atoms, such as, methyl, ethyl, n-propyl or n-butyl; and Z and n have the meanings defined in general Formula I. Illustrative examples of compounds of Formula M are 1-butyl-2[1-(2-dibenzothienyl)ethylimino]pyrrolidine, 2-[1-(2-fluorenyl)ethylimino]hexahydroazepine, 2-[2-methyl-1-(3-phenanthryl)propylimino]octahydroazocine, 2-[1-(2-dibenzofuranyl)propylimino]piperidine, 2-[1-(4-dibenzothienyl)ethylimino]piperidine, 1-methyl-2-[1-(4-dibenzothienyl)ethylimino]hexahydroazapine, 2-[1-(2-fluorenyl)pentylimino]octahydroazonine, 2-[1-(9-phenanthryl)ethyl-imino]hexahydroazepine, 2-[1-(2-phenanthryl)ethylimino]-azacyclotridecane, 2-[1-(9,10-dihydro-2-phenanthryl)-propylimino]azacyclodecane, 2-[1-(2-dibenzothienyl)ethylimino]-N-methyl-hexahydroazepine, 2-[1-(2-dibenzothienyl)-ethylimino]octahydroazocine, 2-[(2-dibenzofuranyl)ethylimino]octahydroazonine, and 2-[1-(3-phenanthryl)ethylimino]azacycloundecane.

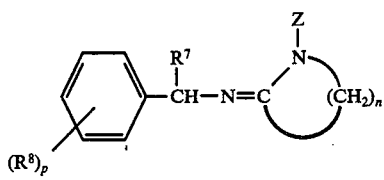

Formula N wherein $R^7$ is a cycloalkyl group of 3 to 5 carbon atoms, such as, cyclopropyl or cyclobutyl; $R^8$ is hydrogen, a lower alkoxy group of from 1 to 4 carbon atoms, such as, methoxy, ethoxy, n-propoxy or n-butoxy, or a lower alkyl group of from 1 to 4 carbon atoms, such as, methyl, ethyl, n-propyl, or n-butyl; p is the integer 1 or 2; and Z and n have the meanings defined in general Formula I. Illustrative examples of compounds of Formula N are 2-[(α-cyclopropylbenzyl)imino]piperidine, 2-[(α-cyclopropyl-α-methoxybenzyl)imino]pyrrolidine, 2-[)α-cyclopropyl-p-butylbenzyl)imino]octahydroazonine, 2[(α-cyclopropyl-tert-butoxybenzyl)imino]hexahydroazepine, 2-[(α-cyclobutylbenzyl)imino]azacyclotridecane, 2-(α-cyclobutyl-2,4-diethylbenzyl)imino]octahydroazocine, 2-[(α-cyclopropylbenzyl)imino]-1-methylpyrrolidine, 2-[(α-cyclopropyl-2,4-dimethylbenzyl)imino]-1-methylhexahydroazepine, 1-ethyl-2-[(α-cyclobutylbenzyl)imino]azacyclodecane, 1-propyl-2-[(α-cyclopentylbenzyl)imino]hexahydroazepine, 2-[(α-cyclobutyl-3,5-dimethoxybenzyl)imino]azacyclododecane, 2-[(α-cyclopentylbenzyl)imino]octahydroazonine, 2-[(α-cyclopentyl-2,4-dipropoxybenzyl)imino]azacyclotridecane, and 2-[(α-cyclopentyl-p-ethoxybenzyl)imino]octahydroazocine.

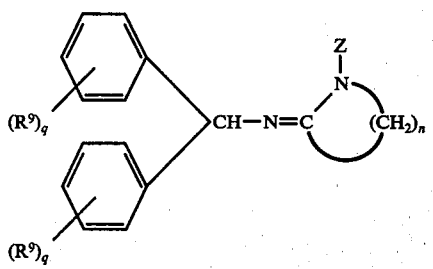

Formula O wherein $R^9$ is hydrogen, a straight or branched lower alkyl group of from 1 to 4 carbon atoms, such as, methyl, ethyl, n-propyl, isopropyl, or n-butyl, chlorine, fluorine, bromine, trifluoromethyl, trifluoromethylthio, trifluoromethoxy, phenyl, phenoxy, or a lower alkoxy group of from 1 to 4 carbon atoms, such as, methoxy, ethoxy, n-propoxy, or n-butoxy; q is an integer of from 1 to 3; and Z and n have the meanings defined in general Formula 1. Illustrative examples of compounds of Formula O are 2-[(bis[p-ethylphenyl]methyl)imino]octahydroazocine, 2-[(p-chloro-α-phenylbenzyl)imino]hexahydroazepine, hexahydro-2-[(α-[m-methylphenyl]-m-isopropylbenzyl)imino]octahydroazonine, 2-[(bis[p-trifluoromethylthiophenyl]methyl)imino]-piperidine, 2-[)m-[trifluoromethyl]α-phenylbenzyl)imino]-hexahydroazepine, 2-[p-chloro-α-[p-chlorophenyl]benzyl)imino]azacyclodecane, 2-[(α-[p-chlorophenyl]-m-trifluoromethylbenzyl)imino]azacycloundecane, 2-[(p-tert-butyl-α-[p-chlorophenyl]benzyl)imino]azacyclododecane, 1-methyl-2-[(α-phenyl-p-trifluoromethoxybenzyl)imino]hexahydroazepine, 2-[(p-bromo-α-phenylbenzyl)imino]azacyclotridecane, 2-[)p-phenoxy-α-phenylbenzyl)imino]azacyclotridecane, 2-[(3,4,5-trimethoxy-α-phenylbenzyl)imino]azacyclododecane, 2-[(3,4-dipropoxy-α-phenylbenzyl)imino]octahydroazonine, 2-[(bis[p-trifluoromethylthiophenyl]methyl)imino]azacyclotridecane, 2-[(diphenylmethyl)imino]-1-methylpiperidine, 2-[(diphenylmethyl)imino]octahydroazocine, 2-[(diphenylmethyl)imino]-N-octahydroazonine, 2-[(m-methoxy-α-phenylbenzyl)imino]hexahydroazepine, 2-[(o-methoxy-α-phenylbenzyl)imino]hexahydroazepine, 2-[(p-butoxy-α-phenylbenzyl)imino]azacyclodecane, 2-[(p-ethoxy-α-phenylbenzyl)imino]-octahydroazonine, and 2-[(diphenylmethyl)imino]azacyclotridecane.

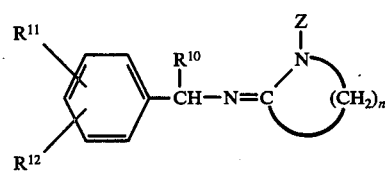

Formula P wherein $R^{10}$ is a lower alkyl group of from 1 to 4 carbon atoms, such as, methyl, ethyl, or n-propyl; $R^{11}$ is hydrogen or a lower alkyl group of from 1 to 4 carbon atoms, such as, methyl, ethyl, or n-butyl; $R^{12}$ is an alkyl group having from 8 to 14 carbon atoms, such as, octyl, nonyl, decyl, dodecyl, tridecyl, or tetradecyl, an alkoxy group having from 8 to 14 carbon atoms, such as, octyloxy, decyloxy, undecyloxy, dodecyloxy, or tetradecyloxy, a cycloalkyl group having from 5 to 14 carbon atoms, such as, cyclopentyl, cycloheptyl, cyclodecyl, cyclododecyl, cyclotetradecyl, or cyclononyl, phenyl, phenoxy, phenylalkyl, wherein the alkyl moiety has from 1 to 4 carbon atoms, such as, methyl, ethyl, or n-propyl, phenylalkoxy wherein the alkoxy moiety has from 2 to 4 carbon atoms, such as, ethoxy or propoxy, 2,2-diphenylvinyl or fluoren-9-ylidene; and Z and n have the meanings defined in general Formula I. Illustrative examples of compounds of Formula P are 2-[(p-decyl-α-methylbenzyl)imino]pyrrolidine, 1-methyl-2-[α-methyl-p-(3,3-diethylpentyl)benzylimino]pyrrolidine, 1-ethyl-2-[p-(dodecyloxy)-α-methylbenzylimino]-piperidine, 2-[α-methyl-p-(3,7-dimethyloctyloxy)benzylimino]piperidine, 1-propyl-2-[α-butyl-p-cyclohexylbenzylimino]hexahydroazepine, 2-[α-methyl-p-cyclododecylbenzylimino]hexahydroazepine, 2-[2,2-diphenylvinyl)-α-isopropylbenzylimino]azacyclodecane, 2-(α-methyl-p-tridecylbenzylimino)hexahydroazepine, 2-[α,2-dimethyl-4-(3-phenoxypropoxy)benzylimino]octahydroazonine, 2-[α,5-dimethyl-2-(3-phenylethoxy)benzylimino]octahydroazocine, 2-[α,3-dimethyl-4-(3-phenylpropoxy)benzylimino]hexahydroazepine, 2-(p-dodecyloxy-2-methylbenzylimino)-hexahydroazepine, 1-methyl-2-[α-methyl-p-phenoxybenzylimino]azacycloundecne, 2-[α-methyl-p-(3-phenyl-1-propen-1-yl)benzylimino]azacyclotridecane, 2-[α-methyl-p-(4-phenylbutoxy)benzylimino]azacyclododecane, and 2-[p-(2-phenoxyethoxy)-α-methylbenzylimino]azacyclotridecane. azacycloundecane

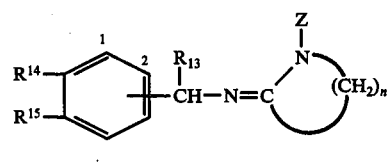

Formula Q wherein $R^{13}$ is a lower alkyl group of from 1 to 4 carbon atoms, such as, methyl, ethyl, n-propyl or n-butyl; $R^{14}$ and $R^{15}$ taken together are $(-CH_2-)_3$, $-CH_2CH_2C(CH_3)_2-$, $-(CH_2)_4-$, or $-C(CH_3)_2CH_2CH_2C(CH_3)_2-$; and Z and $n$ have the meanings defined in general Formula I. Illustrative examples of compounds of Formula O are 1-[1-(1,2,3,4-tetrahydro-6-naphthyl)ethylimino]hexahydroazepine, 2-[1-(4-indanyl)ethylimino]hexahydroazepine, 2-[1-(1,2,3,4-tetrahydro-2,2,4,4-tetramethyl-6-naphthyl)-propylimino]-azacyclotridecane, 1-methyl-2-[1-(4-indanyl)ethylimino]-azacyclododecane, 2-[1-(1,2,3,4-tetrahydro-6-naphthyl)ethylimino]piperidine, 2-[1-(1,1-dimethyl-4-indanyl)ethylimino]azacyclotridecane, and 2-[1-(4-indanyl)ethylimino]pyrrolidine.

The compounds employed in the present invention wherein Z is hydrogen can be prepared by reacting an excess of a lactim ether having the structure

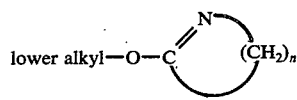

wherein $n$ is an integer of from 3 to 11, and lower alkyl is for example, methyl, ethyl, n-propyl and n-butyl with a primary amine of the formula $R-NH_2$ wherein R has the meaning described in general Formula I in a manner like that reported by R. E. Benson and T. L. Cairns, J. Am. Chem. Soc. 70, 2115-8 (1948). This reaction may be carried out either in the presence or absence of a solvent. When a solvent is used it is preferred that a lower alcohol, such as, methanol or ethanol be used. However, other solvents such as benzene or toluene can be used. A basic or acidic catalyst such as a tertiary amine or hydrogen chloride may be added to the reaction mixture. In general it is preferred that the hydrochloride salt of the amine be used in the reaction. The temperature of the reaction can vary from $-4°$ C to 180° C, and the preferred temperature is about 15° to about 25° C. The reaction time varies from about 1 hour to about 60 days being dependent upon the temperature of the reaction, the reactant primary amine, and more particularly, on the degree of steric hindrance of the amine since highly sterically hindered amines react more slowly.

The lactim ethers which find use in this reaction may be prepared from commercially available corresponding lactams by methods known in the art. For example, by reaction of an appropriate lactam with dimethyl sulfate in a solvent such as benzene, toluene or xylene at the reflux temperature of the solvent for from 2 to 24 hours the corresponding O-methyllactim ether is obtained.

The compounds employed in this invention may also be prepared by using a complex of an appropriate lactam having the structure

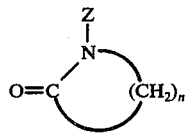

wherein $n$ and Z have the meanings defined in general Formula I with phosphorus oxychloride, phosgene, borontrifluoride etherate, dimethyl sulfate, hydrogen halide or a combination of two or more such reagents. Several attempts have been made to formulate the structure of these complexes, and one formulation includes the vinyl halide, that is, 2-chloro-4,5,6,7-tetrahydro-3H-azepine. However, none of the formulations have been unambiguously established. This reaction has been studied by H. Bredereck in a series of articles in Chem. Ber., 1953-1968, particularly in Vol. 94, 2278 (1961) and Vol. 97, 1403 (1964). The complex formed is reacted with an appropriate primary amine described hereinabove in an aromatic hydrocarbon solvent such as benzene, toluene or xylene or an alkyl polyhalide solvent such as carbon tetrachloride, chloroform, methylene chloride, dichloroethane or tetrachloroethylene. The reaction temperature is limited by the boiling point of the solvent, however, in some cases it is advantageous to carry out the reaction at room temperature or with cooling at 0° to $-40°$ C depending on the reactants.

Similarly the above reaction may be carried out using known thiolactim ethers such as S-methylthiocaprolactim [H. Behringer and H. Neier, Ann. 607, 73-91 (1957)], or by using thiolactams wherein the latter case it may be advantageous to employ a catalyst such as mercury or silver oxide or cyanide [J. Gauthier and J. Renault, C. R. Acad. Sci. 234, (1952)].

The amines, $R-NH_2$, which find use in this invention may be prepared by several known methods or are commercially available or known in the art. The amines wherein R is a straight or branched alkyl group of from 8 to 15 carbon atoms or a lower alkoxyalkyl group wherein the alkyl moiety has from 8 to 15 carbon atoms and the alkoxy moiety has from 1 to 4 carbon atoms are described in U.S. Pat. No. 3,378,438 issued Apr. 16, 1968. Illustrative examples of the preparation of compounds of Formula I wherein R is an alkyl group or a lower alkoxyalkyl group are the following respective Examples 1 and 2.

EXAMPLE 1

2-(Dodecylimino)octahydroazocine

To 28.3 g (0.223 mole) of an enantholactam in 250 ml of benzene is added 34.1 g (0.223 mole) of phosphorous oxychloride over 30 minutes. The mixture is stirred at room temperature for 4 hours after which 41.2 g (0.223 mole) of dodecylamine is added. The reaction mixture is stirred at room temperature for 1 hour and refluxed for 4 hours then allowed to stand overnight. The resulting precipitate is washed with benzene, and the benzene wash is extracted with aqueous 2 N hydrochloric acid and combined with the precipitate. The combined fractions are made alkaline with 2N sodium hydroxide, extracted into ether-methylene chloride, dried and recrystallized from isopropyl alcohol to give 2-dodecyliminooctahydroazocine.

EXAMPLE 2

2-(Ethoxydecylimino)azacyclotridecane

When in the procedure of Example 1 43.9 g (0.223 mole) of azacyclotridecane-2-one is substituted for enantholactam and 44.8 g (0.223 mole) of ethoxydecylamine is substituted for dodecylamine, 2-(ethoxydecylimino)azacyclotridecane is obtained.

When in the procedure of Example 1 appropriate amounts of the following primary amines are substituted for dodecyl amine and appropriate amounts of the following lactams are substituted for enantholactam the respective products listed below are obtained.

| Primary Amine | Lactam | Product |
|---|---|---|
| octylamine | caprylo-lactam | 2-(octylimino)-octahydroazonine |
| 3,7-dimethyloctyl-amine | azacyclo-tridecan-2-one | 2-(3,7-dimethyl-octylimino)aza-cyclotridecane |
| tridecylamine | N-methyl-pyrrolid-2-one | 1-methyl-2-(tri-decylimino)-pyrrolidine |
| methoxyoctylamine | piperid-2-one | 2-(8-methoxyoctyl-imino)piperidine |
| n-butoxytetradecyl-amine | capro-lactam | 2(14-n-butoxy-tetradecylimino)-hexahydroazepine |
| methoxydodecyl-amine | azacyclo-tridecan-2-one | 2-(12-methoxydo-decylimino)azacy-clotridecane |

The amines wherein R is a phenylalkylene group wherein the alkylene moiety has from 1 to 6 carbon atoms and wherein the phenyl moiety is unsubstituted or substituted at the ortho, meta or para-positions where chlorine, fluorine, bromine, lower alkyl of from 1 to 4 carbon atoms, lower alkoxy of from 1 to 4 carbon atoms, hydroxy or methylenedioxy are described, among other places, in Canadian Patent No. 850,116 issued Aug. 25, 1970. An illustrative example of the preparation of a compound of Formula I wherein R is a phenylalkylene group is the following Example 3.

EXAMPLE 3

2-(p-Chlorophenethylimino)hexahydroazepine hydrochloride

A slurry of 15.9 g (0.08 mole) of p-chlorophenethyla-mine hydrochloride in 25 ml of O-methylcaprolactim is allowed to stand at room temperature 3 days with occasional stirring with a glass rod. The mixture is then cooled and the resulting solid is collected, washed with ether and recrystallized from methanol-acetone to give 2-(p-chlorophenylethylimino)hexahydroazapine hydrochloride.

When in the procedure of Example 3 appropriate amounts of the following primary amines are substituted for p-chlorophenethylamine hydrochloride and appropriate amounts of the following O-methyllactims are substituted for O-methylcaprolactim, the respective products listed below are obtained.

| Primary Amine | O-Methyllactim | Product |
|---|---|---|
| phenylpropylamine HCl | O-methylcapryl-lactim | 2-(phenylpro-pylimino(octa-hydroazonine HCl |
| p-hydroxyphenyl-pentylamine HCl | O-methylval-erolactim | 2-(p-hydroxy-phenylpentyl-imino)piperi-dine HCl |
| 3,4-methylenedi-oxyphenethylamine HCl | O-methyllauryl-lactim | 2-(3',4'-meth-ylenedioxyphen-ethylimino)aza-cyclotridecane HCl |

The amines wherein R is an α-(1- or 2-naphthylben-zyl) or a 1- or 2-naphthylalkylene group wherein the alkylene moiety has from 1 to 6 carbon atoms which is straight or branched and wherein the naphthalene moiety is unsubstituted or mono- or di- substituted with chlorine, fluorine, bromine, trifluoromethyl, an alkyl group having from 1 to 12 carbon atoms which is straight or branched, an alkoxy group having from 1 to 3 carbon atoms or NO$_2$ are described in U.S. Pat. No. 3,894,002, issued July 8, 1975, particularly at column 5, line 30 to 45, and their reaction with appropriate O-lower alkyl-lactims, lactams or S-lower alkyl-lactims at column 4, lines 49 to 65, column 5, lines 1 to 29 and lines 46 to 52 and in specific Examples 4 to 29 which portions and Examples of said patent are incorporated herein by reference thereto.

The amines wherein R is 1- or 2-adamantyl, or 1- or 2-norbornyl are described in U.S. Pat. No. 3,838,151, issued Sept. 24, 1974 particularly at column 3, lines 27 to 30 and their reaction with appropriate O-lower alkyl-lactims, lactams or S-lower alkyl-lactims at column 2, lines 64 to 71, column 3 at lines 1 to 26 and lines 30 to 37 and in specific Examples 1 to 7 which portions and Examples of said patent are incorporated herein by reference thereto.

The amines wherein R is 9-fluorenyl which is unsubstituted or substituted in which case the substituents may be attached to any one of the 4 available carbon atoms of each aromatic ring and are chlorine, fluorine, bromine, a lower alkyl group having from 1 to 4 carbon atoms, a lower alkoxy group having from 1 to 4 carbon atoms or NO$_2$ are described in U.S. Pat. No. 3,873,520 issued Mar. 25, 1975, particularly in column 4 at lines 49 to 62 and Example 12 and their reaction with appropriate O-lower alkyl-lactims, S-lower alkyl-lactims, or lactams, in column 3 at lines 53 to 68, column 4 at lines 1 to 33, lines 42 to 48, lines 63 to 68, in column 5 at lines 1 to 17, and in specific Examples 1 to 11 and 13 to 16 which portions and Examples of said patent are incorporated herein by reference thereto.

The amine wherein R is dibenzocyclohepten-5-yl is commercially available. The reaction of this amine with appropriate O-lower alkyl-lactims, S-lower alkyl-lactims or lactams is described in U.S. Pat. No. 3,833,559 issued Sept. 3, 1974, particularly at column 3, lines 21 to 25, lines 54 to 75, column 4 at lines 1 and 2 and in specific Examples 1 to 4 which portions and Examples of said patent are incorporated herein by reference thereto.

The amine wherein R is 1-benzylcyclopentyl is known in the art. The reaction of this amine with O-lower alkylbutyrolactims is described in U.S. Pat. No. 3,803,170 issued Apr. 9, 1974, in column 2 at lines 39 to 67 and in Example 1 which portion and Example of said patent are incorporated herein by reference thereto.

The amines wherein R is

wherein X is oxygen or sulfur, A is a bond or an alkylene chain having from 1 to 3 carbon atoms, and R$^1$ is hydrogen, a straight or branched lower alkyl group having from 1 to 4 carbon atoms, a straight or branched lower alkenyl group having from 3 to 6 carbon atoms, a cycloalkyl group having from 3 to 6 carbon atoms, or phenyl are described in U.S. Pat. No. 3,816,457 issued June 11, 1974, particularly at column 4, lines 41 to 65 and their reaction with appropriate O-lower alkyl-lactims, lactams, S-lower alkyl-lactims at column 4, lines 1 to 40, lines 66 to 75, column 5 at lines 1 to 25 and in specific Examples 1 to 22 which portions and Examples of said patent are incorporated herein by reference thereto. The preparation of compounds of this type wherein Z is a lower alkyl group of from 1 to 4 carbon atoms can be prepared from a suitably N-substituted lactam as described hereinabove.

The amines wherein R is

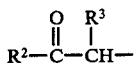

wherein $R^2$ is phenyl or a cycloalkyl group having from 3 to 6 carbon atoms, and $R^3$ is hydrogen or methyl are disclosed in U.S. Pat. No. 3,845,071 issued Oct. 29, 1974, particularly at column 4, lines 71 to 75 and column 5 at lines 1 and 2 and their reaction with appropriate O-lower alkyl-lactims containing from 4 to 8 cyclic carbon atoms is described at column 4, lines 30 to 62 and in specific Examples I to V which portions and Examples of said patent are incorporated herein by reference thereto. Compounds used herein wherein R is

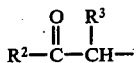

and $n$ is an integer of from 8 to 11 can be prepared by the general procedure described hereinabove and in U.S. Pat. No. 3,845,071 by substituting an appropriate O-lower alkyl-lactim ether wherein $n$ is from 8 to 11 for the lactim ethers wherein $n$ is from 3 to 7, or by the general procedures described hereinabove using an appropriate lactam or S-lower alkyl-lactim ether.

The amines wherein R is

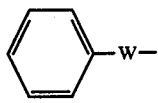

wherein W is a straight or branched divalent alkylene chain having from 2 to 6 carbon atoms which is substituted with 1 phenyl group on any of the 6 carbon atoms with the proviso that the carbon atom adjacent to the exocyclic nitrogen atom must have at least 1 hydrogen attached thereto are described in U.S. Pat. No. 3,852,269 issued Dec. 3, 1974, particularly at column 4, lines 7 to 25 and there reaction with appropriate O-lower alkyl-lactims, lactams or S-lower alkyl-lactims wherein the lactim or lactam ring has from 4 to 8 cyclic carbon atoms is described at column 3, lines 29 to 68, column 4 at lines 1 to 6 and lines 26 to 66 and in specific Examples 1 to 10 which portions and Examples of said patent are incorporated herein by reference thereto. Compounds having this diphenylalkylene substituent wherein the lactamimide ring has from 9 to 12 cyclic carbon atoms, that is, wherein $n$ is an integer of from 8 to 11 which lactamimide ring may be unsubstituted on the cyclic nitrogen atom or substituted thereon with a lower alkyl group may be prepared as described hereinabove and as generally described in U.S. Pat. No. 3,852,265 using an appropriate O-lower alkyl-lactim, lactam or S-lower alkyl-lactim.

The amines wherein R is

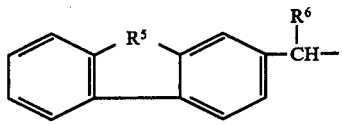

wherein $R^5$ is oxygen, sulfur, —$CH_2$—, —$CH_2CH_2$— or —$CH=CH$—, and $R^6$ is hydrogen or a lower alkyl group of from 1 to 4 carbon atoms are described in U.S. Pat. No. 3,840,523 issued Oct. 8, 1974, particularly at column 4, lines 27 to 43 and Example 1 and their reaction with appropriate O-lower alkyl-lactims, lactams or S-lower alkyl-lactims, at column 3, lines 59 to 75, column 4 at lines 1 to 18 and lines 44 to 70 and in specific Examples I to X which portions and Examples of said patent are incorporated herein by reference thereto. The amines wherein R is

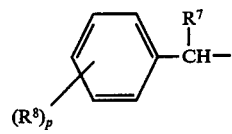

wherein $R^7$ is a cycloalkyl group of from 3 to 5 carbon atoms, $R^8$ is hydrogen, lower alkoxy of from 1 to 4 carbon atoms or lower alkyl of from 1 to 4 carbon atoms and $p$ is the integer 1 or 2 are described in U.S. Pat. No. 3,840,524 issued Oct. 8, 1974, at column 5, lines 52 to 60 and their reaction with O-lower alkyl-lactims having from 4 to 10 cyclic carbon atoms and wherein the cyclic nitrogen atom is unsubstituted and lactams having from 4 to 10 cyclic carbon atoms wherein the cyclic nitrogen atom is unsubstituted or substituted with methyl is described at column 4, lines 57 to 76, column 5 at lines 1 to 37, and in specific Examples ii to XII which portions and Examples of said patent are incorporated herein by reference thereto. Compounds prepared using this amine wherein Z is an alkyl group of from 2 to 4 carbon atoms or wherein the lactamimide ring has 11 or 12 cyclic carbon atoms, that is, wherein $n$ is 10 or 11 can be prepared as described hereinabove using an appropriate O-lower alkyl-lactim ether, lactam or S-lower alkyl-lactim ether.

The amines wherein R is

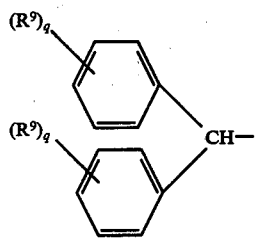

wherein one of $R^9$ is hydrogen and the other of $R^9$ is hydrogen or lower alkoxy of from 1 to 4 carbon atoms and $q$ is the integer 1 are described in U.S. Pat. No. 3,783,162 issued Jan. 1, 1974, particularly at column 5, lines 67 and 68, column 6 at lines 1 to 34 and in specific Examples 2A and 3 and their reaction with appropriate O-lower alkyl-lactim ethers, lactams or S-lower alkyl-lactim ethers is described at column 4, lines 39 to 68, column 5 at lines 1 to 52 and in specific Examples 1, 2B, and 4 to 11 which portions and Examples of said patent are incorporated herein by reference thereto.

The amines wherein R is

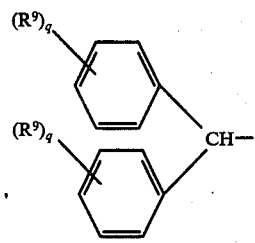

wherein q is an integer of from 1 to 3, and R is a straight or branched lower alkyl group of from 1 to 4 carbon atoms, chlorine, fluorine, bromine, trifluoromethyl, trifluoromethylthio, trifluoromethoxy, phenyl, phenoxy or a lower alkoxy group of from 1 to 4 carbon atoms with the proviso that both R groups are not hydrogen and with the proviso that when q is equal to 1 and one of the R groups is hydrogen, the other R group is not lower alkoxy of from 1 to 4 carbon atoms are described in U.S. application Ser. No. 391,573 filed Aug. 27, 1973, for which a Notice of Allowance was mailed Jan. 28, 1976, on page 8, line 10 through page 9, line 5, page 12 at lines 7 to 30, page 13 at lines 1 and 2 and in specific Example 2A and their reaction with appropriate O-lower alkyl-lactim ethers, lactams or S-lower alkyl-lactim ethers having from 4 to 8 cyclic carbon atoms wherein the nitrogen atom is unsubstituted is described on page 7 at lines 4 to 24, page 8 at lines 1 and 2, page 9 at lines 8 to 25, page 10 at lines 1 to 12, page 11 at lines 10 to 30, and in specific Examples 1, 2B and 3 to 20 which portions and specific Examples of said patent application are incorporated herein by reference thereto. Compounds having an amine of this type wherein the lactamimide ring has from 9 to 12 cyclic carbon atoms or wherein the cyclic nitrogen atom is substituted with a lower alkyl group can be prepared as described hereinabove using the appropriate lactim ether or lactam. The amines wherein R is

wherein $R^{10}$ is a lower alkyl group of from 1 to 4 carbon atoms, $R^{11}$ is hydrogen or lower alkyl of from 1 to 4 carbon atoms, $R^{12}$ is an alkyl group having from 8 to 14 carbon atoms, an alkoxy group having from 8 to 14 carbon atoms, a cycloalkyl group having from 5 to 14 carbon atoms, phenyl, phenoxy, phenylalkyl wherein the alkyl moiety has from 1 to 4 carbon atoms, phenylalkoxy wherein the alkoxy moiety has from 2 to 4 carbon atoms, 2,2-diphenylvinyl or fluoren-9-ylidene or wherein R is

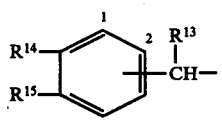

wherein $R^{13}$ is a lower alkyl group of from 1 to 4 carbon atoms, and $R^{14}$ and $R^{15}$ taken together are —(CH$_2$)$_3$—, —CH$_2$LCH$_2$C(CH$_3$)$_2$—, —(CH$_2$)$_4$— or —C(CH$_3$)$_2$—CH$_2$CH$_2$C(CH$_3$)$_2$— can be prepared by several known methods. These amines can be obtained by the Leuckart reaction whereby the appropriate acetophenone derivative is heated with ammonium formate at from about 165° to 195° C for from 2 to 12 hours followed by acid hydrolysis, to form the desired amine. The alkyl, cyclohexyl, phenyl, phenoxy or phenylalkyl substituted acetophenone may be obtained by a standard Friedel-Crafts acylation of the appropriately substituted benzene derivative. The alkoxy, phenylolkoxy, phenoxyalkoxy substituted acetophenone may be obtained by reaction of 2', 3', or 4'-hydroxyacetophenone with alkyl, phenylalkyl or phenoxyalkyl halide in the presence of a base. Alternatively, the acetophenones may be obtained by reaction of methyl magnesium halide with an appropriately substituted benzonitrile. The Grignard complex formed may also be reduced in situ with lithium aluminum hydride to the amine avoiding the Leuckart reaction. Illustrative examples of the preparation of amines of this type and of compounds employed in the present invention having amines of this type are the following.

EXAMPLE 4

α-Methyl-p-phenethylbenzylamine hydrochloride

A mixture of 87.5 g (0.39 mole) of 4'-phenethylacetophenone, M.P. 67°–70° C., prepared according to R. E. Lutz et al., J. Org. Chem. 12, 617 (1947), and 98.5 g (1.56 mole) of ammonium formate is slowly heated to 150° C. with stirring. After the initial foaming has subsided the temperature of the heating bath is raised to 185°–190° C. for a period of 4 hours. Upon cooling, the mixture is treated with several portions of water. To the residue is added 75 ml of concentrated HCl. The mixture is refluxed for 2 hours and is allowed to cool. The resulting solid is collected, washed with several portions of benzene and is recrystallized from isopropanol containing about 5% of water to yield 74.0 g (73% yield) of the desired product, M.P. 212°–214° C.

Following essentially the same procedure but substituting for the 4'-phenethylacetophenone an appropriate molar amount of the following ketones, results in the formation of the amine-hydrochlorides indicated:

TABLE I

| Ketone | Amine Hydrochloride | M.P. |
|---|---|---|
| 4'-Tridecyl-acetophenone | α-Methyl-p-tridecyl-benzylamine | 110 – 2° C |
| 4'Dodecyloxy-acetophenone | p-Dodecyloxy-α-methylbenzylamine | 99 – 112° C |
| 4'-Cyclohexyl-acetophenone | p-Cyclohexyl-α-methylbenzylamine | 232 – 6° C (dec.) |
| 4'-Phenyl-acetophenone | α-Methyl-p-phenyl-benzylamine | 223 – 6° C |
| 4'-Phenoxy-acetophenone | α-Methyl-p-phenoxy-benzylamine | 196 – 9° C |
| 4'-(2,2-Di-phenylvinyl)-acetophenone | p-(2,2-Diphenylvinyl)-α-methylbenzylamine | 238 – 42° C |
| 4-Acetyl-1,1-dimethyl-6-tert.-butylindane | 4-(α-Aminoethyl)-1,1-dimethyl-6-tert-butylindane | 254 – 5° C (dec.) |
| 7-Acetyl-6-ethyl-1,1,4,4-tetramethyl-1,2,3,4-tetrahydronaphthalene | 7-(α-Aminoethyl)-6-ethyl-1,1,4,4-tetramethyl-1,2,3,4-tetrahydronaphthalene | 261 – 3° C (dec.) |

EXAMPLE 5

4'-(3-Phenylpropoxy)acetophenone

A mixture of 68.1 g (0.5 mole) of 4'-hydroxyacetophenone, 100.3 g (0.5 mole) of a 3-phenylpropyl bromide, 69.0 g (0.5 mole) of potassium carbonate and 500 ml of anhydrous acetone is refluxed with stirring for 8 hours. After adding 1 liter of water the product is extracted into ether, the extract is washed with water and 2 N sodium carbonate solution and dried over anhydrous sodium sulfate and the solvent is evaporated. The resulting oil (125.8 g) begins to crystallize and yields after two recrystallizations from ether-hexane and ether, respectively, 73.9 g (58% yield) of the desired product, M.P. 80°–81°.

Following essentially the same procedure, the following reactants are substituted for the 4'-hydroxyacetophenone and 3-phenylpropyl bromide: 4'-hydroxyacetophenone and 3-phenoxypropyl bromide 3'-hydroxyacetophenone and 4-phenoxybutyl bromide 2'-hydroxyacetophenone and phenethyl bromide, resulting in the formation of the following products, respectively: 4'-(3-phenoxypropoxy)acetophenone, M.P. 78–79° C., 3'-(4-phenoxybutoxy)acetophenone, M.P. 60°–61° C., and 2'-(2-phenylethoxy)acetophenone, M.P. 40°–43° C.

EXAMPLE 6 p-(Fluoren-9-ylidenemethyl)-α-methyl-benzylamine hydrochloride

A hot solution of 100.0 g of α-fluoren-9-ylidene-p-tolunitrile, prepared as described by R. E. Allen et al., J. Amer. Chem. Soc. 80, 591 (1958), in 2 liter of toluene is added rapidly to methylmagnesium iodide (prepared from 82.0 g of methyl iodide in ethyl ether) in 1 liter of toluene. After refluxing for 2 hours, the mixture is decomposed with 3 N HCl. The crude product is recrystallized from acetonitrile to yield 87.1 g (82% yield) of 4'-fluoren-9-ylidenylmethylacetophenone, M.P. 123°–126° C.

Following essentially the same procedure as in Example 4 but substituting 4'-fluoren-9-ylidenylmethylacetophenone for the 4'-phenethylacetophenone results in the formation of p-(fluoren-9-ylidenemethyl)-α-methylbenzylamine hydrochloride having a M.P. 259°–61° C.(dec.).

EXAMPLE 7

Hexahydro-2-(α-methyl-p-phenethylbenzylimino)-azepine hydrochloride

A mixture of 15.0 g of α-methyl-p-phenethylbenzylamine hydrochloride and 25 ml of O-methylcaprolactim is stirred into a slurry and allowed to stand at room temperature for 4 days with occasional stirring. Small portions of absolute ethanol are added to keep the slurry stirrable. The mixture is then cooled to −20° C., the precipitate is collected, washed with small portions of absolute ether and recrystallized from a mixture of acetone-methanol to yield 15.7 g (76% yield) of the desired product, M.P. 230°–231° C.

EXAMPLE 8

2-(α-Methyl-p-tridecylbenzylimino)hexahydro-1H-azepine hydrochloride

Following essentially the same procedure described in Example 7 but substituting α-methyl-p-tridecylbenzylamine hydrochloride for the α-methyl-p-phenethylbenzylamine hydrochloride above, results in the formation of 2-(α-methyl-p-tridecylbenzylimino)hexahydroazepine hydrochloride having a M.P. 183°–5° C.

EXAMPLE 9

2-(p-Dodecyloxy-α-methylbenzylimino)-hexahydro-1H-azepine hydrochloride

Following essentially the same procedure described in Example 7 above and substituting p-dodecyloxy-α-methylbenzylamine hydrochloride for the α-methyl-p-phenyethylbenzylamine hydrochloride above, results in the formation of 2-(p-dodecyloxy-α-methylbenzylimino)hexahydroazepine hydrochloride having a M.P. of 186°–8° C (dec.).

EXAMPLE 10

2-(p-Cyclohexyl-α-methylbenzylimino)hexahydro-1H-azepine hydrochloride

Following essentially the same procedure described in Example 7 above and substituting p-cyclohexyl-α-methylbenzylamine hydrochloride for the α-methyl-p-phenyethylbenzylamine hydrochloride above, results in the formation of 2-(p-cyclohexyl-α-methylbenzylimino)-hexahydroazepine hydrochloride having a M.P. of 245°–7° C.

EXAMPLE 11

2-[α-(4-Biphenylyl)ethylimino]hexahydro-1H-azepine hydrochloride

Following essentially the same procedure described in Example 7 above and substituting α-methyl-p-phenylbenzylamine hydrochloride for the α-methyl-p-phenylbenzylamine hydrochloride above, results in the formation of 2-[α-(4-biphenylyl)ethylimino]hexahydroazepine hydrochloride having a M.P. of 245°–7° C.

EXAMPLE 12

2-(α-Methyl-p-phenoxybenzylimino)hexahydro-1H-azepine-hydrochloride

Following essentially the same procedure described in Example 7 above and substituting α-methyl-p-phenoxybenzylamine hydrochloride for the α-methyl-p-phenethylbenzylamine hydrochloride above, results in the formation of 2-(α-methyl-p-phenoxybenzylimino)hexahydroazepine hydrochloride having a M.P. of 210°–2° C., (dec.).

EXAMPLE 13

2-[p-(2,2-Diphenylvinyl)-α-methylbenzylimino]-hexahydro-1H-azepine hydrochloride Following essentially the same procedure described in Example 7 above and substituting p-(2,2-diphenylvinyl)-α-methylbenzylamine hydrochloride for the α-methyl-p-phenethylbenzylamine hydrochloride above, results in the formation of 2-[p-(2,2-diphenylvinyl)-α-methylbenzylimino]hexahydroazepine hydrochloride having a M.P. of 219°–21° C.

EXAMPLE 14

2-[1-(6-tert.-Butyl-1,1-dimethyl-4-indanyl)-ethylimino]-hexahydro-1H-azepine hydrochloride Following essentially the same procedure described in Example 7 above and substituting 4-(α-aminoethyl)-1,1-dimethyl-6-tert.-butylindane for the α-methyl-p-phenethylbenzylamine hydrochloride above, results in the formation of 2-[1-(6-tert.-butyl-1,1-dimethyl-4-indanyl)-ethylimino]hexahydro-1H-azepine hydrochloride, having a M.P. of 257°–8° C. (dec.).

EXAMPLE 15

2-[1-(7-Ethyl-1,2,3,4-tetrahydro-1,1,4,4-tetramethyl-6-naphthyl)ethylimino]hexahydro-1H-azepine hydrochloride Following essentially the same procedure described in Example 7 above and substituting 7-(α-aminoethyl(-6-ethyl-1,1,4,4-tetramethyl-1,2,3,4-tetrahydronaphthalene for the α-methyl-p-phenethylbenzylamine hydrochloride above, results in the formation of 2-[1-(7-ethyl-1,2,3,4-tetrahydro-1,1,4,4-tetramethyl-6-naphthyl)ethylimino]-hexahydro-1H-azepine hydrochloride, having a M.P. of 246.5°-7.5° C. (dec.).

EXAMPLE 16

Hexahydro-2-[α-methyl-p-(3-phenylpropoxy)benzylimino]azepine hydrochloride

Following essentially the same procedure described in Example 4 above but substituting 4'-(3-phenylpropoxy)-acetophenone for the 4'-phenethylacetophenone results in the formation of p-(3-phenylpropoxy)-α-methylbenzylamine hydrochloride, M.P. 142°-5° C.

Substituting this amine for the α-methyl-p-phenethylbenzylamine of Example 7 results in the formation of hexahydro-2-[α-methyl-p-(3-phenylpropoxy)benzylimino]-azepine hydrochloride, having a M.P. of 202°-5° C.

EXAMPLE 17

Hexahydro-2-[α-methyl-p-(3-phenoxypropoxy)benzylimino]azepine hydrochloride

Following essentially the same procedure described in Example 4 above but substituting 4'-(3-phenoxypropoxy)-acetophenone for the 4'-phenethylacetophenone results in the formation of α-methyl-p-(3-phenoxypropoxy)benzylamine hydrochloride, M.P. 71°-81° C.

Substituting this amine for the α-methyl-p-phenethylbenzylamine of Example 7 results in the formation of hexahydro-2-[α-methyl-p-(3-phenoxypropoxybenzylimino]-azepine hydrochloride, having a M.P. of 162°-4° C.

EXAMPLE 18

2-[α-Methyl-m-(4-phenoxybutoxy)benzylimino]pyrrolidine hydrochloride

Following essentially the same procedure described in Example 4 above but substituting 3'-(4-phenoxybutoxy)-acetophenone for the 4'-phenethylacetophenone results in the formation of α-methyl-m-(4-phenoxybutoxy)benzylamine hydrochloride, M.P. 79°-81° C.

Substituting this amine for the α-methyl-p-phenethylbenzylamine hydrochloride, and substituting O-methylbutyrolactim for the O-methylcaprolactim results in the formation of 1-[α-methyl-m-(4-phenoxybutoxy)benzylimino]-pyrrolidine hydrochloride, having a M.P. of 136°-8° C. (dec.).

EXAMPLE 19

Hexahydro-2-[α-methyl-o-(2-phenylethoxy)benzylimino]-azepine hydrochloride

Following essentially the same procedure described in Example 4 above but substituting 2'-(2-phenylethoxy)-acetophenone for the 4'-phenethylacetophenone results in the formation of α-methyl-o-(2-phenylethoxy)-benzylamine hydrochloride, M.P. 120°-133° C. (dec.).

Substituting this amine for the α-methyl-p-phenethylbenzylamine of Example 7 results in the formation of hexahydro-2-[α-methyl-o-(2-phenylethoxy)benzylimino]-azepine hydrochloride, having a M.P. of 189°-90° C. (dec.).

EXAMPLE 20

1-Methyl-2-(α-methyl-p-phenethylbenzylimino)-pyrrolidine hydrochloride

To 9.9 g (0.1 mole) of N-methyl-2-pyrrolidine in 200 ml of benzene is added dropwise 7.7 g (0.05 mole) of phosphorous oxychloride. The mixture is stirred at room temperature for a period of 4 hours. α-Methyl-p-phenethylbenzylamine hydrochloride, 13.1 g (0.05 mole), is added, the mixture stirred at room temperature for 1 hour and at its reflux temperature for an additional period of 4 hours. After cooling overnight, 2 N hydrochloric acid is added, the benzene layer separated and the aqueous layer made alkaline with 2 N NaOH. The product is extracted with ether, dried and upon removal of the solvent yielded 15.5 g of oil which is converted into its hydrochloride salt by the addition of HCl. After three recrystallizations from acetone, 5.8 g of the desired product is obtained, M.P. 87°-89° C.

EXAMPLE 21

2-[α-(4-Biphenylyl)ethylimino]azacyclotridecane hydrochloride

To 5.0 g (25 m mole) of 2-azatridecanone in 100 ml of benzene is added dropwise 3.9 g (25 m mole) of phosphorous oxychloride and the mixture stirred at room temperature for a period of 4 hours. α-Methyl-p-phenylbenzylamine hydrochloride, 5.3 g (23 m mole), is added and stirred at room temperature for 1 hour and refluxed for an additional 4 hours. Hydrochloric acid, 2N, is added and the benzene layer separated, dried over sodium sulfate, and evaporated to dryness. The crude product is crystallized from acetone, M.P. 135°-142° C.

EXAMPLE 22

2-[1-[p-(Fluoren-9-ylidenemethyl)phenyl]ethylimino]-hexahydro-1H-azepine

Following essentially the same procedure described in Example 7 above and substituting 4'-fluoren-9-ylidenylmethylacetophenone for the α-methyl-p-phenethylbenzylamine hydrochloride above results in the formation of 2-[1-[p-(fluoren-9-ylidenemethyl)phenyl]ethylimino]-hexahydro-1H-azepine, having a M.P. of 265.5°-7.5° C (dec.).

The amines wherein R is

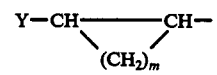

wherein m is an integer of from 1 to 6 and Y is 2-thienyl, a cycloalkyl group having from 5 to 7 carbon atoms, a phenyl group which is unsubstituted or substituted at the ortho, meta, or para-positions with chlorine, fluorine, bromine, a lower alkyl group having from 1 to 4 carbon atoms or a lower alkoxy group having from 1 to 4 carbon atoms may be prepared by several known methods. The substituted cycloalkyl amine may be obtained from the corresponding nitro derivative or the oxime (C. Kaiser et al, J. Med. Pharm. Chem. 5, 1243

(1962)) by reduction. Or the cyclohexylcycloalkylamine compounds may be obtained by hydrogenation of the corresponding phenylcycloalkylamine derivatives. Also by the Leuckart reaction the appropriately substituted cycloalkanone is heated with ammonium formate to a temperature of 165°–200° C for from 2 to 12 hours to give the desired substituted cycloalkylamine. The substituted cycloalkanone derivatives may be obtained by a Grignard reaction of a suitable aryl-or cycloalkyl magnesium halide with an appropriate cycloalkanone to give the corresponding substituted cycloalkanone which is subsequently treated with hydrogen peroxide by methods generally known in the art. The following examples are illustrative preparations of amines of this type and of compounds employed in the present invention substituted with amines of this type.

EXAMPLE 23

Hexahydro-2-[(cis-2-phenylcyclopentyl)imino]-azepinehydrochloride

A mixture of 4.0 g of cis-2-phenylcyclopentylamine hydrochloride, M.P. 205°–206° C and 5.0 ml of O-methylcaprolactim is allowed to stand at room temperature for 6 days with occasional stirring. A few drops of ethanol are added to maintain a stirrable slurry, after which the mixture is cooled. The resulting solid is washed with ether and recrystallized from acetone/methanol to give the desired product, M.P. 181.5°–183.5° C (dec.).

EXAMPLE 24

Hexahydro-2-[(trans-2-phenylcyclopentyl)imino]-azepinehydrochloride

Following the procedure of Example 23, only substituting for cis-2-phenylcyclopentylamine hydrochloride the appropriate molar equivalent amount of trans-2-phenylcyclopentylamine hydrochloride, M.P. 147°–149° C, the desired product is obtained, M.P. 192°–195° C.

EXAMPLE 25

2-[(cis-2-Cyclohexylcyclopentyl)imino]hexahydroazepinehydrochloride

A. Using rhodium-on-charcoal catalyst in a Paar shaker, 12.6 g of cis-2-phenylcyclopentylamine hydrochloride, M.P. 204°–206° C in 100 ml of water is hydrogenated. In 20 hours when the theoretical amount of hydrogen has been taken up the catalyst is removed by filtration, the filtrate made basic with sodium hydroxide solution, and the resulting precipitate is extracted into ether. After evaporation of the ether the residue is distilled, M.P. 100°–102° C (6.0 mm). The hydrochloride salt is prepared and recrystallized from isopropanol-ether to give 4.4 g of cis-2-(cyclohexyl)cyclopentylamine hydrochloride, M.P 174°–176° C.

B. By the procedure of Example 23, only employing a reaction time of 29 days and substituting for cis-2-phenylcyclopentylamine hydrochloride an appropriate amount of cis-2-cyclohexylcyclopentylamine hydrochloride, the desired product is obtained, M.P. 179°–180° C.

EXAMPLE 26

2-[(trans-2-Cyclohexylcyclopentyl)imino]hexahydroazepine hydrochloride

By the procedure described in Example 25(A) only substituting for cis-2-phenylcyclopentylamine hydrochloride an appropriate amount of trans-2-phenylcyclopentylamine hydrochloride, M.P. 142°–143° C, the hydrochloride salt of trans-2-cyclohexylcyclopentylamine is obtained, M.P. 199°–200° C. Following the procedure of Example 23 only substituting for cis-2-phenylcyclopentylamine hydrochloride and appropriate amount of trans-2-cyclohexylcyclopentylamine hydrochloride and employing a reaction time of 38 days, the desired product is obtained, M.P. 208°–210° C.

EXAMPLE 27

2-[2-{p-Chlorophenyl}cyclopentyl)imino]hexahydroazepine hydrochloride

From 575 g of p-chlorophenyl bromide and 78 g of magnesium turnings in 2.6 liters of anhydrous ether is prepared p-chlorophenyl magnesium bromide to which is added dropwise a solution of 252 g of cyclopentanone in in 1 liter of ether. The mixture is stirred overnight and is decomposed by careful addition of dilute hydrochloric acid. The organic phase is separated, washed and dried, and the solvent is evaporated. The resulting solid is recrystallized from ethanol to give 316 g of 1-(p-chlorophenyl)cyclopentene, M.P. 71°–73° C, which was dissolved in 2.9 liters of acetic acid containing 6 ml of concentrated sulfuric acid. To this solution 133 g of 50% hydrogen peroxide is added dropwise during which time the reaction temperature is maintained at 30° to 33° C. The reaction temperature is maintained at 30° to 35° C. The reaction mixture is stirred overnight after which water is added and the product is extracted into ether. The extract is washed, dried and the solvent evaporated leaving crude 2-(p-chlorophenyl)cyclopentanone which distilled, B.P. 135°–154° C (0.1 mm) yielding 140 g. The oxime, M.P. 154°–155° C prepared by reaction with hydroxylamine hydrochloric acid is reduced using Raney nickel in alcoholic ammonia to give 1-(p-chlorophenyl)cyclopentylamine which is subsequently converted to the hydrochloride salt, M.P. 226°–228° C. Following the procedure of Example 23, only substituting for cis-2-phenylcyclopentylamine hydrochloride, an appropriate amount of 2-(p-chlorophenyl)-cyclopentylamine hydrochloride, the desired product is obtained, M.P. 253°–255° C.

EXAMPLE 28

Following the procedure of Example 23, only substituting for O-methylcaprolactim an appropriate amount of o-methylenantholactim, O-methylcaprylolactim, O-methylvalerolactim of O-methylbutylcaprolactim, the following compounds are obtained:

octahydro-2-[(cis-2-phenylcyclopentyl)imino]azocine hydrochloride, octahydro-2-[(cis-2-phenylcyclopentyl)-imino]azonine hydrochloride, M.P. 207°–209° C, 2-[(cis-2-phenylcyclopentyl)imino]piperidine hydrochloride, M.P. 173°–176° C, hexahydro-2-[(cis-2-phenylcyclopentyl)imino]azepine hydrochloride.

EXAMPLE 29

Hexahydro-2-[(trans-2-phenylcyclohexyl)imino]azepine hydrochloride

Following the procedure of Example 23, only substituting for cis-2-phenylcyclopentylamine hydrochloride an appropriate amount of trans-2-phenylcyclohexylamine hydrochloride, M.P. 251°–257° C, and employing a reaction time of 38 days, the desired product is obtained, M.P. 236°–239° C.

By the procedure of Example 23, only substituting for cis-2-phenylcyclopentylamine hydrochloride an appropriate amount of the hydrochloride salt of an amine listed in Table I, the respective products listed in Table I are obtained. The amines employed in Examples 30 through 34 are described by W. F. Trager et al., in J. Org. Chem. 27, 3006–10 (1962), and those used in Examples 35 and 36 are described by M. Mousseron and M. Mousseron-Canet, C.R. Acad. Sci. 239, 502 (1954). The amines employed in Examples 37 and 38 are obtained by the reduction of 2-(m-anisyl)cyclohexanone oxime and 2-(p-anisyl)cyclohexanone oxime [W. C. and R. B. Wildman, J. Org. Chem. 17, 581 (1952)] and those used in Examples 39 and 40 are obtained by the reduction of the oxime of 2-cyclopentylcyclopentanone (H. Cristol et al., Bull Soc. Chim. France 1958, 556).

TABLE II

| Example No. | Amine | Final Product |
|---|---|---|
| 30 | 2-(o-tolyl)cyclohexylamine | hexahydro-2-[2-({o-tolyl}cyclohexyl)imino]azepine hydrochloride |
| 31 | 2-(p-tolyl)cyclohexylamine | hexahydro-1-[2-({p-tolyl}cyclohexyl)imino]azepine hydrochloride |
| 32 | 2-(o-chlorophenyl)-cyclopropylamine | 2-[2-({o-chlorophenyl}-cyclopropyl)imino]hexahydroazepine hydrochloride |
| 33 | 2-(m-chlorophenyl)-cyclohexylamine | 2-[2-({m-chlorophenyl}-cyclohexyl)imino]hexahydroazepine hydrochloride |
| 34 | 2-(p-chlorophenyl)-cyclohexylamine | 2-[2-({p-chlorophenyl}-cyclohexyl)imino]hexahydroazepine hydrochloride |
| 35 | cis-2-cyclopentylcyclohexylamine | 2-[2-({cis-2-cyclopentyl}cyclohexyl)imino]-hexahydroazepine hydrochloride |
| 36 | trans-2-cyclopentylcyclohexylamine | 2-[2-({trans-2-cyclopentyl}cyclohexyl)imino]hexahydroazepine-hydrochloride |
| 37 | 2-(m-anisyl)cyclohexylamine | 2-[2-({m-anisyl}cyclohexyl)imino]hexahydroazepine hydrochloride |
| 38 | 2-(p-anisyl)cyclobutylamine | 2-[2-({p-anisyl}cyclobutyl)imino]hexahydroazepine hydrochloride |
| 39 | cis-2-(cyclopentyl)cyclopentylamine | 2-[2-({cis-2-cyclopentyl}cyclopentyl)imino]-hexahydroazepine hydrochloride |
| 40 | trans-2-(cyclopentyl)-cyclopentylamine | 2-[2-({trans-2-cyclopentyl}cyclopentyl)imino]hexahydroazepine-hydrochloride |

EXAMPLE 41

Hexahydro-2-[(2-{2-thienyl}cyclopentyl)imino]azepine hydrochloride

By the procedure described in U.S. Pat. No. 2,520,516 (1950) 2-(2-thienyl)cyclopentylamine hydrochloride, M.P. 168°–172° C is prepared and substituted for cis-2-phenylcyclopentylamine hydrochloride in Example 23 to give the desired product, M.P. 144°–151° C.

EXAMPLE 42 cis- and trans-Hexahydro-2[(2-phenylcycloheptyl)imino]azepine hydrochloride

Following the procedure of Example 23 only substituting for cis-2-phenylcyclopentylamine hydrochloride an appropriate amount of cis- or trans-2-phenylcycloheptylamine hydrochloride, M.P. 229°–230° C and 199°–201° C respectively, the desired products are obtained, cis-M.P. 234°–235° C, trans- M.P. 207°–211° C.

EXAMPLE 43

2-[(cis-2-Cyclohexylcyclopentyl)imino]piperidine hydrochloride

Following the procedure of Example 23, only substituting for cis-2-phenylcyclopentylamine hydrochloride and O-methylcaprolactim, appropriate amounts of cis-2-(cyclohexyl)cyclopentylamine hydrochloride and O-methylvalerolactim respectively the desired product is obtained, M.P. 195.5°–197° C.

EXAMPLE 44

2-[(cis-2-Phenylcyclopentyl)imino]azacyclotridecane hydrochloride

To 21.7 g of 2-azacyclotridecanone in 200 ml of dry benzene is added dropwise 15.3 g of phosphorus oxychloride. The mixture is stirred at room temperature for 4 hours after which 19.8 g of cis-2-phenylcyclopentylamine hydrochloride is added. The reaction mixture is stirred at room temperature for 2 hours and refluxed for 24 hours. The resulting homogeneous solution is washed with 2N NaOH, 2N HCl and saturated NaCl solution, dried over sodium sulfate and the solvent evaporated. The resulting oily product crystallized from acetone is recrystallized from methanol-acetone to give the desired product, M.P. 156°–159° C.

EXAMPLE 45

By the procedure of Example 44 only substituting for 2-azacyclotridecanone an appropriate amount of 2-pyrrolidone or caprolactam the following products are obtained: 2-[(cis-2-phenylcyclopentyl)imino]pyrrolidine hydrochloride, and 2[(cis-2-phenylcyclopentyl)imino]hexahydroazepine hydrochloride.

The amines wherein R is ortho, meta or para-biphenyl are commercially available or can be prepared by methods known in the art as described, for example, in Ind. Eng. Chem. 22, 31–4 (1930), J. Soc. Chem. Ind. 49, 15T (1930) and J. Am. Chem. Soc. 68, 1663 (1946). The following examples illustrate the preparation of compounds employed in the present invention wherein R is ortho, meta, or parabiphenylamine.

EXAMPLE 46

2-(o-Biphenylylimino)azacyclotridecane hydrochloride

To 43.5 g (0.22 mole) of 2-azacyclotridecanone in 200 ml of dry benzene is added dropwise 30.7 g (0.2 mole) of phosphorousoxychloride. The reaction mixture is stirred at room temperature for 4 hours after which 33.8 g (0.2 mole) of o-biphenylamine is added and stirring is continued at room temperature for 1 hour then at reflux temperature for 4 hours. The reaction mixture is alowed to stand overnight then is washed with 2N hydrochloric acid, dried and evaporated leaving a residue which is recrystallized from acetone/methanol to give 2-(o- biphenylylimino)azacyclotridecane hydrochloride, M.P. 249°-251° C.

When in the procedure of Example 46 appropriate amounts of the amines and lactams listed below are substituted respectively for o-biphenylamine and 2-azacyclotridecanone the respective products listed below are obtained:

| Amine | Lactam | Product |
|---|---|---|
| o-biphenylamine | enantholactam | 2-(o-biphenyl-imino)octahydro-azonine |
| m-biphenylamine | caprolactam | 2-(m-biphenylyl-imino)hexahydro-azepine |
| p-biphenylamine | valerolactam | 2-(p-biphenylyl-imino)piperidine |
| o-biphenylamine | butyrolactam | 2-(o-biphenylyl-imino)pyrrolidine |
| p-biphenylamine | 2-azacyclotri-decanone | 2-(p-biphenylyl-imino)azacyclo-tridecane |

Compounds employed in the present invention wherein R is 1- or 2-adamantanyl or 1- or 2-norbornyl or dibenzocyclohepten-5-yl and the cyclic nitrogen atom of the lactamimide ring is substituted with a lower alkyl group of from 1 to 4 carbon atoms can be prepared by reacting the appropriate R-substituted amine with an appropriate lactam as generally described hereinabove.

The term lower alkoxyalkyl wherein the alkoxy moiety has frm 1 to 4 carbon atoms and the alkyl moiety has from 8 to 15 carbon atoms as used in general Formulas I and A is taken to mean a group of the structure $C_nH_{2n'+1}$—O-C-di m'$H_{2m'}$—0 wherein $n'$ is an integer of from 1 to 4, and $m'$ is an integer of from 8 to 15.

The substituent A' as used in general Formulas I and C is benzyl, that is

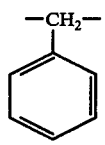

or a straight or branched alkylene group of from 1 to 6 carbon atoms wherein the carbon atom attached to the exocyclic nitrogen atom of the lactamimide moiety has at least one hydrogen atom attached to it.

Illustrative examples of pharmaceutically acceptable salts which may be formed of the compounds employed in the present invention are those of any suitable inorganic acids, such as, hydrochloric, hydrobromic, sulfuric or phosphoric acids or any suitable organic acid, such as, carboxylic acids, such as, acetic, propionic, glycolic, lactic, pyruvic, malonic, succinic, fumaric, malic, tartaric, citric, ascorbic, maleic, hydroxymaleic, benzoic, hydroxybenzoic, phenylacetic, cinnamic, salicyclic, 2-phenoxybenzoic, or sulfonic acids, such as, methane sulfonic or 2-hydroxyethane sulfonic acid.

We claim:

1. A method of treating gastrointestinal hypersecretion in a patient in need thereof which comprises administering to said patient a gastrointestinal hypersecretion inhibitory effective amount of a compound of the formula

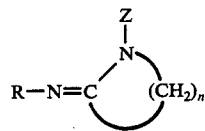

wherein

Z is hydrogen or lower alkyl of from 1 to 4 carbon atoms;

$n$ is an integer of from 5 to 11; and R is a straight or branched alkyl group of from 8 to 15 carbon atoms; or a lower alkoxyalkyl group wherein the alkyl moiety has from 8 to 15 carbon atoms and the alkoxy moiety has from 1 to 4 carbon atoms; a phenylalkylene group wherein the alkylene moiety has from 1 to 6 carbon atoms and wherein the phenyl moiety is unsubstituted or substituted in which case the substituents may be attached at the ortho, meta or para-position of the phenyl ring and are chlorine, fluorine, bromine, lower alkyl having from 1 to 4 carbon atoms, lower alkoxy having from 1 to 4 carbon atoms, or hydroxy;

the group

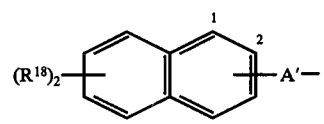

wherein A' is a straight or branched alkylene moiety of from 1 to 6 carbon atoms or benzyl and is attached to either the 1- or 2-position of the naphthalene ring, and $R^{18}$ is hydrogen, chlorine, fluorine, bromine, trifluoromethyl, an alkyl group having from 1 to 12 carbon atoms which is straight or branched, an alkoxy group having from 1 to 3 carbon atoms or $NO_2$;

1- or 2-adamantyl; 1- or 2-norbornyl;

ortho, meta, or para-biphenylyl;

9-fluorenyl which is unsubstituted or substituted in which case the substituents may be attached to any one of the four available carbon atoms of each aromatic ring and are chlorine, bromine, fluorine, a lower alkyl group having from 1 to 4 carbon atoms, a lower alkoxy group having from 1 to 4 carbon atoms, or $NO_2$;

dibenzocyclohepten-5-yl;

the group

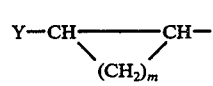

wherein $m$ is an integer of from 1 to 6, and Y is a cycloalkyl group having from 5 to 7 carbon atoms, a phenyl group which is unsubstituted or substituted in which case the substituents may be attached to the ortho, meta, or para-position of the phenyl ring and are chlorine, fluorine, bromine, a lower alkyl group having from 1 to 4 carbon atoms or a lower alkoxy group having from 1 to 4 carbon atoms;

the group

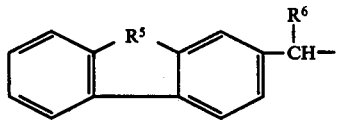

wherein R² is phenyl or a cycloalkyl group having from 3 to 6 carbon atoms, and R³ is hydrogen or methyl;
the group

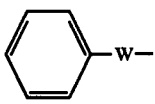

wherein W is a straight or branched divalent alkylene chain having from 2 to 6 carbon atoms which is substituted with one phenyl group on any of the 6 carbon atoms with the proviso that the carbon atom adjacent to the exocyclic nitrogen atom must have at least one hydrogen attached to it;
the group

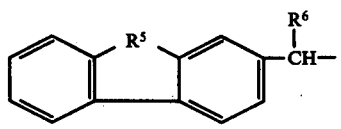

wherein R⁵ is —CH₂—, —2CH₂— or —CH=λCH—, and R⁶ is hydrogen or a lower alkyl group of from 1 to 4 carbon atoms;
the group

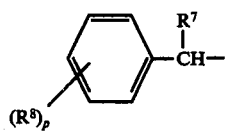

wherein R⁷ is cycloalkyl of from 3 to 5 carbon atoms, R⁸ is hydrogen, lower alkoxy of from 1 to 4 carbon atoms or lower alkyl of from 1 to 4 carbon atoms, and p is the integer 1 or 2;
the group

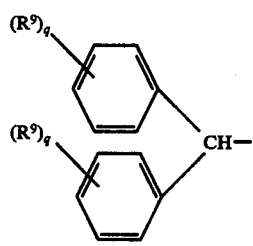

wherein R⁹ is hydrogen, a straight or branched lower alkyl group of from 1 to 4 carbon atoms, chlorine, fluorine, bromine, CF₃, SCF₃, OCF₃, phenyl, phenoxy or a lower alkoxy group of from 1 to 4 carbon atoms and q is an integer of from 1 to 3;
the group

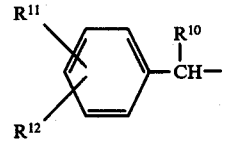

wherein R¹⁰ is a lower alkyl group of from 1 to 4 carbon atoms, R¹¹ is hydrogen or lower alkyl of from 1 to 4 carbon atoms, R¹² is an alkyl group having from 8 to 14 carbon atoms, an alkoxy group having from 8 to 14 carbon atoms, a cycloalkyl group having from 5 to 14 carbon atoms, phenyl, phenoxy, phenylalkyl wherein the alkyl moiety has from 1 to 4 carbon atoms, phenylalkoxy wherein the alkoxy moiety has from 2 to 4 carbon atoms, 2,2-diphenylvinyl or fluoren-9-ylidene; or
the group

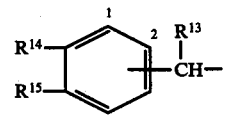

wherein the phenyl moiety is attached to the

moiety through the 1- or 2-position of the phenyl ring, R¹³ is a lower alkyl group of from 1 to 4 carbon atoms and R¹⁴ and R¹⁵ taken together are (—CH₂—)₃, —CH₂CH₂C(CH₃)₂—, —(CH₂)₄— or —C(CH₃)₂CH₂CH₂C(CH₃)₂—; with the proviso that when R is the group

Z is hydrogen; and pharmaceutically acceptable acid addition salts thereof or individual optical or geometric isomers.

2. The method of claim 1 wherein n is the integer 11.

3. The method of claim 1 wherein R is a straight or branched alkyl group of from 8 to 15 carbon atoms or a lower alkoxyalkyl group wherein the alkyl moiety has from 8 to 15 carbon atoms and the alkoxy moiety has from 1 to 4 carbon atoms.

4. The method of claim 3 wherein n is the integer 11.

5. The method of claim 1 wherein R is phenylalkylene wherein the alkylene moiety has from 1 to 6 carbon atoms and wherein the phenyl moiety is unsubstituted or substituted at the ortho, meta or para-position of the phenyl ring with chlorine, bromine, fluorine, lower alkyl of from 1 to 4 carbon atoms, lower alkoxy of from 1 to 4 carbon atoms, hydroxy or methylenedioxy.

6. The method of claim 5 wherein n is the integer 11.

7. The method of claim 1 wherein R is

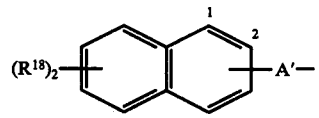

wherein A' is a straight or branched alkylene moiety of from 1 to 6 carbon atoms or benzyl and is attached to either the 1- or 2-position of the naphthalene ring, and $R^{18}$ is hydrogen, chlorine, fluorine, bromine, trifluoromethyl, an alkyl group having from 1 to 12 carbon atoms which is straight or branched, an alkoxy group having from 1 to 3 carbon atoms or $NO_2$.

8. The method of claim 7 wherein $n$ is the integer 11.

9. The method of claim 7 wherein the compound is hexahydro-2-[1-(1-naphthyl)ethylimino]azepine or a pharmaceutically acceptable salt thereof.

10. The method of claim 1 wherein R is 1- or 2-adamantyl or 1- or 2-norbornyl.

11. The method of claim 10 wherein $n$ is the integer 11.

12. The method of claim 10 wherein the compound is 2-(1-adamantylimino)hexahydroazepine or a pharmaceutically acceptable salt thereof.

13. The method of claim 1 wherein R is 9-fluorenyl which is unsubstituted or substituted at any one of the 4 available carbon atoms of each aromatic ring with chlorine, bromine, fluorine, a lower alkyl group of from 1 to 4 carbon atoms, a lower alkoxy group of from 1 to 4 carbon atoms or $NO_2$.

14. The method of claim 13 wherein $n$ is the integer 11.

15. The method of claim 13 wherein the compound is 2-(9-fluoroenylimino)hexahydroazepine or a pharmaceutically acceptable salt thereof.

16. The method of claim 1 wherein R is dibenzocyclohepten-5-yl.

17. The method of claim 16 wherein $n$ is the integer 11.

18. The method of claim 16 wherein the compound is 2-[(10,11-dihydro-5H-dibenzo[a,d]cyclohepten-5-yl)imino]hexahydroazepine or a pharmaceutically salt thereof.

19. The method of claim 1 wherein R is 1-benzylcyclopentyl.

20. The method of claim 1 wherein R is

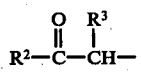

wherein $R^2$ is phenyl or cycloalkyl having from 3 to 6 carbon atoms, and $R^3$ is hydrogen or methyl.

21. The method of claim 20 wherein $n$ is the integer 11.

22. The method of claim 20 wherein the compound is 2-(hexahydroazepine-2-ylidenamino)propiophenone or a pharamceutically acceptable salt thereof.

23. The method of claim 1 wherein R is

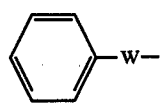

wherein W is a straight or branched divalent alkylene chain having from 2 to 6 carbon atoms which is substituted with one phenyl group on any one of the 6 carbon atoms with the proviso that the carbon atom adjacent to the exocyclic nitrogen atom must have at least 1 hydrogen attached thereto.

24. The method of claim 23 wherein $n$ is the integer 11.

25. The method of claim 23 wherein the compound is hexahydro-2-[(2,2-diphenylpentyl)imino]azepine or a pharmaceutically acceptable salt thereof.

26. The method of claim 1 wherein R is

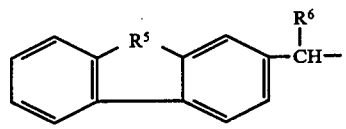

wherein $R^5$ is $-CH_2-$, $-CH_2CH_2-$ or $CH=CH-$, and $R^6$ is hydrogen or lower alkyl of from 1 to 4 carbon atoms.

27. The method of claim 26 wherein $n$ is the integer 11.

28. The method of claim 1 wherein R is

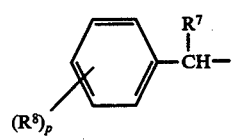

wherein $R^7$ is cycloalkyl of from 3 to 5 carbon atoms, $R^8$ is hydrogen, lower alkoxy of from 1 to 4 carbon atoms or lower alkyl of from 1 to 4 carbon atoms, and $p$ is the integer 1 or 2.

29. The method of claim 28 wherein $n$ is the integer 11.

30. The method of claim 28 wherein the compound is 2-[(α-cyclopropyl-2,4-dimethylbenzyl)imino]octahydroazonine or a pharmaceutically acceptable salt thereof.

31. The method of claim 1 wherein R is

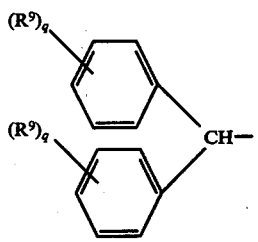

wherein $R^9$ is hydrogen, a straight or branched lower alkyl group of from 1 to 4 carbon atoms, chlorine, fluorine, bromine, trifluoromethyl, trifluoromethylthio, trifluoromethoxy, phenyl, phenoxy, or a lower alkoxy group of from 1 to 4 carbon atoms, and $q$ is an integer of from 1 to 3.

32. The method of claim 31 wherein $n$ is the integer 11.

33. The method of claim 31 wherein the compound is hexahydro-2-[(m-[trifluoromethyl]-α-phenylbenzyl)imino]-azepine or a pharmaceutically acceptable salt thereof.

34. The method of claim 1 wherein R is

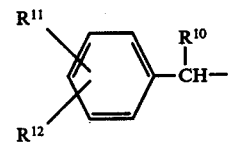

wherein $R^{10}$ is a lower alkyl group of from 1 to 4 carbon atoms, $R^{11}$ is hydrogen or lower alkyl of from 1 to 4 carbon atoms, and $R^{12}$ is an alkyl group having from 8 to 14 carbon atoms, an alkoxy group having from 8 to 14 carbon atoms, a cycloalkyl group having from 5 to 14 carbon atoms, phenyl, phenoxy, phenylalkyl wherein the alkyl moiety has from 1 to 4 carbon atoms, phenylalkoxy wherein the alkoxy moiety has from 2 to 4 carbon atoms, 2,2-diphenylvinyl or fluoren-9-ylidene.

35. The method of claim 34 wherein $n$ is the integer 11.

36. The method of claim 34 wherein the compound is 2-(α-methyl-p-phenoxybenzylimino)hexahydroazepine or a pharmaceutically acceptable salt thereof.

37. The method of claim 1 wherein R is

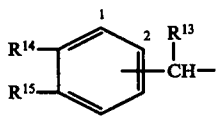

wherein the phenyl moiety is attached to the

moiety through the 1- or 2-position of the phenyl ring, $R^{13}$ is a lower alkyl group of from 1 to 4 carbon atoms, and $R^{14}$ and $R^{15}$ taken together are (—CH$_2$—)$_3$, —CH$_2$CH$_2$C(CH$_3$)$_2$—, (—CH$_2$—)$_4$, or —C(CH$_3$)$_2$CH$_2$CH$_2$C(CH$_3$)$_2$—.

38. The method of claim 37 wherein $n$ is the integer 11.

39. The method of claim 1 wherein R is

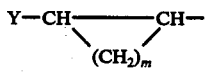

wherein $n$ is an integer of from 1 to 6 and Y is a cycloalkyl group having from 5 to 7 carbon atoms, a phenyl group which is unsubstituted or substituted at the ortho, meta or para-position with chlorine, fluorine, bromine, a lower alkyl group of from 1 to 4 carbon atoms or a lower alkoxy group of from 1 to 4 carbon atoms.

40. The method of claim 39 wherein $n$ is the integer 11.

41. The method of claim 39 wherein the compound is 2-[(2-cyclohexylcyclopentyl)imino]hexahydroazepine or a pharmaceutically acceptable salt thereof.

42. The method of claim 39 wherein the compound is 2-[cis-2-phenylcyclopentyl)imino]azacyclotridecane or a pharmaceutically acceptable salt thereof.

43. The method of claim 1 wherein R is ortho, meta or para-biphenylyl.

44. The method of claim 43 wherein $n$ is the integer 11.

45. The method of claim 43 wherein the compound is 2-(o-biphenylylimino)azacyclotridecane or a pharmaceutically acceptable salt thereof.

46. A method of treating gastric hypersecretion in a patient in need thereof which comprises administering to said patient a gastric hypersecretion inhibitory effective amount of a compound of the formula

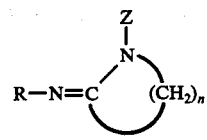

wherein
Z is hydrogen or lower alkyl of from 1 to 4 carbon atoms;
$n$ is an integer of from 5 to 11; and R is a straight or branched alkyl group of from 8 to 15 carbon atoms; or a lower alkoxyalkyl group wherein the alkyl moiety has from 8 to 15 carbon atoms and the alkoxy moiety has from 1 to 4 carbon atoms; a phenylalkylene group wherein the alkylene moiety has from 1 to 6 carbon atoms and wherein the phenyl moiety is unsubstituted or substituted in which case the substituents may be attached at the ortho, meta or para-position of the phenyl ring and are chlorine, fluorine, bromine, lower alkyl having from 1 to 4 carbon atoms, lower alkoxy having from 1 to 4 carbon atoms, or hydroxy;
the group

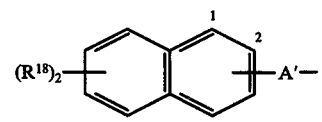

wherein A' is a straight or branched alkylene moiety of from 1 to 6 carbon atoms or benzyl and is attached to either the 1- or 2-position of the naphthalene ring, and $R^{18}$ is hydrogen, chlorine, fluorine, bromine, trifluoromethyl, an alkyl group having from 1 to 12 carbon atoms which is straight or branched, an alkoxy group having from 1 to 3 carbon atoms or NO$_2$;
1- or 2-adamantyl; 1- or 2-norbornyl; ortho, meta or para-biphenylyl; 9-fluorenyl which is unsubstituted or substituted in which case the substituents may be attached to any one of the four available carbon atoms of each aromatic ring and are chlorine, bromine, fluorine, a lower alkyl group having from 1 to 4 carbon atoms, a lower alkoxy group having from 1 to 4 carbon atoms or NO$_2$;
dibenzocyclohepten-5-yl;
the group

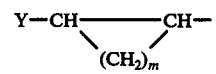

wherein $m$ is an integer of from 1 to 6, and Y is a cycloalkyl group having from 5 to 7 carbon atoms, a phenyl group which is unsubstituted or substituted in which case the substituents may be attached to the ortho, meta, or para-position of the phenyl ring and are chlorine, fluorine, bromine, a lower alkyl group having from 1 to 4 carbon atoms or a lower alkoxy group having from 1 to 4 carbon atoms;
the group

wherein $R^2$ is phenyl or a cycloalkyl group having from 3 to 6 carbon atoms, and $R^3$ is hydrogen or methyl;
the group

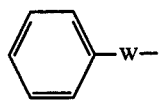

wherein W is a straight or branched divalent alkylene chain having from 2 to 6 carbon atoms which is substituted with one phenyl group on any of the 6 carbon atoms with the proviso that the carbon atom adjacent to the exocyclic nitrogen atom must have at least one hydrogen attached to it;
the group

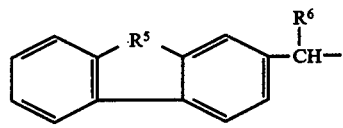

wherein $R^5$ is —$CH_2$—, —$CH_2CH_2$— or —CH=CH—, and $R^6$ is hydrogen or a lower alkyl group of from 1 to 4 carbon atoms;
the group

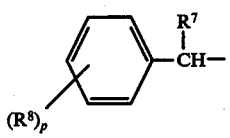

wherein $R^7$ is cycloalkyl of from 3 to 5 carbon atoms, $R^8$ is hydrogen, lower alkoxy of from 1 to 4 carbon atoms or lower alkyl of from 1 to 4 carbon atoms, and p is the integer 1 or 2;
the group

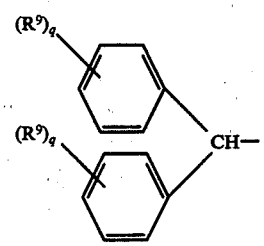

wherein $R^9$ is hydrogen, a straight or branched lower alkyl group of from 1 to 4 carbon atoms, chlorine, fluorine, bromine, $CF_3$, $SCF_3$, $OCF_3$, phenyl, phenoxy or a lower alkoxy group of from 1 to 4 carbon atoms and q is an integer of from 1 to 3;
the group

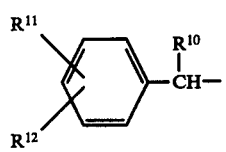

wherein $R^{10}$ is a lower alkyl group of from 1 to 4 carbon atoms, $R^{11}$ is hydrogen or lower alkyl of from 1 to 4 carbon atoms, $R^{12}$ is an alkyl group having from 8 to 14 carbon atoms, an alkoxy group having from 8 to 14 carbon atoms, a cycloalkyl group having from 5 to 14 carbon atoms, phenyl, phenoxy, phenylalkyl wherein the alkyl moiety has from 1 to 4 carbon atoms, phenylalkoxy wherein the alkoxy moiety has from 2 to 4 carbon atoms, 2,2-diphenylvinyl or fluoren-9-ylidene; or the group

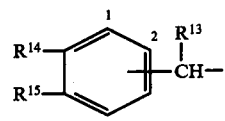

wherein the phenyl moiety is attached to the

moiety through the 1- or 2-position of the phenyl ring, $R^{13}$ is a lower alkyl group of from 1 to 4 carbon atoms and $R^{14}$ and $R^{15}$ taken together are (—$CH_2$—)$_3$, —$CH_2CH_2C(CH_3)_2$, —($CH_2$)$_4$— or —$C(CH_3)_2CH_2CH_2C(CH_3)_2$—; with the proviso that when R is the group

Z is hydrogen, and pharmaceutically acceptable acid addition salts thereof or individual optical or geometric isomers.

47. The method of claim 46 wherein n is the integer 11.

48. A method of treating intestinal hypersecretion in a patient in need thereof which comprises administering to said patient an intestinal hypersecretion inhibitory effective amount of a compound of the formula

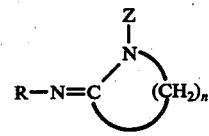

wherein
Z is hydrogen or lower alkyl of from 1 to 4 carbon atoms;
n is an integer of from 5 to 11; and
R is a straight or branched alkyl group of from 8 to 15 carbon atoms; or a lower alkoxyalkyl group wherein the alkyl moiety has from 8 to 15 carbon atoms and the alkoxy moiety has from 1 to 4 carbon atoms; a phenylalkylene group wherein the alkylene moiety has from 1 to 6 carbon atoms and wherein the phenyl moiety is unsubstituted or substituted in which case the substituents may be attached at the ortho, meta or para-position of the phenyl ring and are chlorine, fluorine, bromine, lower alkyl having from 1 to 4 carbon atoms, lower alkoxy having from 1 to 4 carbon atoms, or hydroxy;
the group

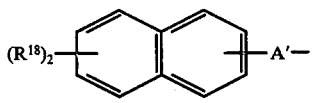

wherein A' is a straight or branched alkylene moiety of from 1 to 6 carbon atoms or benzyl and is attached to either the 1- or 2-position of the naphthalene ring, and $R^{18}$ is hydrogen, chlorine, fluorine, bromine, trifluoromethyl, an alkyl group having from 1 to 12 carbon atoms which is straight or branched, an alkoxy group having from 1 to 3 carbon atoms or $NO_2$; 1- or 2-adamantyl; 1- or 2-norbornyl; ortho, meta or parabiphenylyl; 9-fluorenyl which is unsubstituted or substituted in which case the substituents may be attached to any one of the four available carbon atoms of each aromatic ring and are chlorine, bromine, fluorine, a lower alkyl group having from 1 to 4 carbon atoms, a lower alkoxy group having from 1 to 4 carbon atoms or $NO_2$;
dibenzocyclohepten-5-yl;
the group

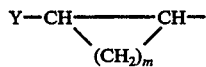

wherein m is an integer of from 1 to 6, and Y is a cycloalkyl group having from 5 to 7 carbon atoms, a phenyl group which is unsubstituted or substituted in which case the substituents may be attached to the ortho, meta, or para-position of the phenyl ring and are chlorine, fluorine, bromine, a lower alkyl group having from 1 to 4 carbon atoms or a lower alkoxy group having from 1 to 4 carbon atoms;
the group

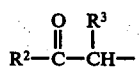

wherein $R^2$ is phenyl or a cycloalkyl group having from 3 to 6 carbon atoms, and $R^3$ is hydrogen or methyl;
the group

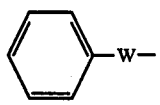

wherein W is a straight or branched divalent alkylene chain having from 2 to 6 carbon atoms which is substituted with one phenyl group on any of the 6 carbon atoms with the proviso that the carbon atom adjacent to the exocyclic nitrogen atom must have at least one hydrogen attached to it;
the group

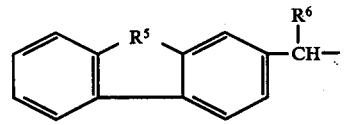

wherein $R^5$ is —$CH_2$—, —$CH_2CH_2$— or —CH=CH—, and $R^6$ is hydrogen or a lower alkyl group of from 1 to 4 carbon atoms;
the group

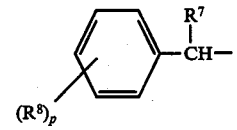

wherein $R^7$ is cycloalkyl of from 3 to 5 carbon atoms, $R^8$ is hydrogen, lower alkoxy of from 1 to 4 carbon atoms, and p is the integer 1 or 2.
the group

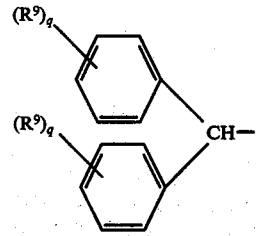

wherein $R^9$ is hydrogen, a straight or branched lower alkyl group of from 1 to 4 carbon atoms, chlorine, fluorine, bromine, $CF_3$, $SCF_3$, $OCF_3$, phenyl, phenoxy or a lower alkoxy group of from 1 to 4 carbon atoms and q is an integer of from 1 to 3;
the group

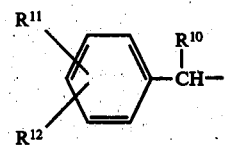

wherein $R^{10}$ is a lower alkyl group of from 1 to 4 carbon atoms, $R^{11}$ is hydrogen or lower alkyl of from 1 to 4 carbon atoms, $R^{12}$ is an alkyl group having from 8 to 14 carbon atoms, an alkoxy group having from 8 to 14 carbon atoms, a cycloalkyl group having from 5 to 14 carbon atoms, phenyl, phenoxy, phenylalkyl wherein the alkyl moiety has from 1 to 4 carbon atoms, phenylalkoxy wherein the alkoxy moiety has from 2 to 4 carbon atoms, 2,2-diphenylvinyl or fluoren-9-ylidene; or
the group

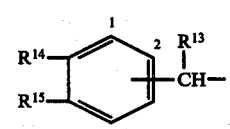

wherein the phenyl moiety is attached to the moiety through the 1- or 2-position of the phenyl ring, $R^{13}$ is a lower alkyl group of from 1 to 4 carbon atoms and $R^{14}$ and $R^{15}$ taken together are $(-CH_2-)_3$, $-CH_2CH_2C(CH_3)_2-$, $-(CH_2)_4-$ or $-C(CH_3)_2CH_2CH_2C(CH_3)_2-$; with the proviso that when R is the group

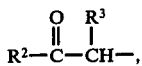

Z is hydrogen, and pharmaceutically acceptable acid addition salts thereof or individual optical or geometrical isomers.

49. The method of claim 48 wherein $n$ is the integer 11.

50. The method of claim 1 wherein the compound is 2-[(diphenylmethyl)imino]azacyclotridecane, or a pharmaceutically acceptable salt thereof.

51. The method of claim 1 wherein the compound is 2-[1-(1-naphthyl)ethylimino]azacyclotridecane, or a pharmaceutically acceptable salt thereof.

* * * * *

UNITED STATES PATENT AND TRADEMARK OFFICE
CERTIFICATE OF CORRECTION

PATENT NO. : 4,061,746

DATED : December 6, 1977

INVENTOR(S) : T.R.Blohm, J.M.Grisar and N.L. Wiech

It is certified that error appears in the above-identified patent and that said Letters Patent are hereby corrected as shown below:

Column 2, line 7 "1- or 2-norborny;" should read -- 1- or 2-norbornyl; --; line 20, that portion of the formula reading "Y-CH——CH-" (with $(CH_2)_m$ bridge) should read -- Y-CH——CH- (with $(CH_2)_m$ bridge) --. Column 8, line 64 "azcyclotridecane" should read -- azacyclotridecane --. Column 14, line 61 "azacyclotridecane. azacycloundecane" should read -- azacyclotridecane --. Column 15, line 7 "Formula O" should read -- Formula Q --. Column 20, line 33 "Examples ii" should read -- Examples II --. Column 21, line 66 "-$CH_2LCH_2C(CH_3)_2$-" should read -- -$CH_2CH_2C(CH_3)_2$- --. Column 22, line 10 "2°,3'-" should read --2',3'- --. Column 24, line 31 "phenylbenzylamine" should read -- phenethylbenzylamine --. Column 28, line 6 "and" should read -- an --; line 51 "of" should read -- or --. Column 30, line 65 "alowed" should read -- allowed --; line 66 "2N hydrochloric acid" should read -- 2N sodium hydroxide and with 2N hydrochloric acid --. Column 31, lines 19-20, 1st Column "p-biphenylamine decanone" should read -- p-biphenylamine- lines 19-20, 2nd Column "2-azacyclotri-imino) azacyclo" should read -- 2-azacyclotridecanone --; lines 19 - 21, 3rd Column "2-(p-biphenyltridecane" should read -- 2-(p-biphenylylimino)- azacyclotridecane --; line 31 "frm" should read -- from --; line 34 "$C_{n'}H_{2n'+1}$-O-C-di m'$H_{2m'}$-O" should read -- $C_{n'}H_{2n'+1}$-O-$C_{m'}H_{2m'}$- Column 32, line 55 "Y-CH——CH-" (with $(CH_2)_m$ bridge) should read -- Y-CH——CH- (with $(CH_2)_m$ bridge) --

UNITED STATES PATENT AND TRADEMARK OFFICE
CERTIFICATE OF CORRECTION

PATENT NO. : 4,061,746
DATED : December 6, 1977
INVENTOR(S) : T.R.Blohm, J.M.Grisar and N.L.Wiech It is certified that error appears in the above-identified patent and that said Letters Patent are hereby corrected as shown below:

Column 33, line 5, that portion of the formula which reads 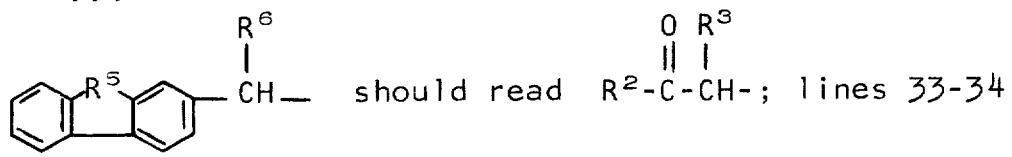 should read $R^2-\overset{O}{\overset{\|}{C}}-\overset{R^3}{\overset{|}{CH}}-$; lines 33-34 "-2CH$_2$- or -CH=λ CH-" should read -- -CH$_2$-CH$_2$- or -CH=CH- --. Column 35, line 28 "2-(9-fluoroenylimino)" should read -- 2-(9-fluorenylimino) --. Column 37, line 40 "Y-CH————CH-"
$\diagdown$(CH$_2$)$_m$$\diagup$ should read -- Y-CH————CH- --;
$\diagdown$(CH$_2$)$_m$$\diagup$ Column 38, line 50 "Y-CH————CH-"
$\diagdown$(CH$_2$)$_m$$\diagup$ should read -- Y-CH————CH- --. Column 41, line 30
$\diagdown$(CH$_2$)$_m$$\diagup$

UNITED STATES PATENT AND TRADEMARK OFFICE
CERTIFICATE OF CORRECTION

PATENT NO. : 4,061,746

DATED : December 6, 1977

INVENTOR(S) : T.R.Blohm, J.M.Grisar and N.L.Wiech

It is certified that error appears in the above-identified patent and that said Letters Patent are hereby corrected as shown below:

$$\text{"Y-CH} \underset{(CH_2)_m}{\diagdown \diagup} \text{CH-" should read -- Y-CH} \underset{(CH_2)_m}{\diagdown \diagup} \text{CH- --.}$$

Signed and Sealed this

Fourteenth Day of November 1978

[SEAL]

Attest:

RUTH C. MASON
Attesting Officer

DONALD W. BANNER
Commissioner of Patents and Trademarks